US006955802B1

(12) United States Patent
Jessell et al.

(10) Patent No.: US 6,955,802 B1
(45) Date of Patent: Oct. 18, 2005

(54) HOMEODOMAIN PROTEIN CODE SPECIFYING PROGENITOR CELL IDENTIFY AND NEURONAL FATE IN THE VENTRAL NEURAL TUBE

(75) Inventors: Thomas M. Jessell, Bronx, NY (US); James Briscoe, London (GB); Johan Ericson, Hasselby (SE)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/569,259

(22) Filed: May 11, 2000

(51) Int. Cl.$^7$ ............................ A61K 49/00; C12N 5/00; C12N 5/02; C12N 5/08
(52) U.S. Cl. ........................... 424/9.2; 424/9.1; 435/325; 435/366; 435/368; 435/377
(58) Field of Search ................................. 435/325, 366, 435/368, 377; 424/9.1, 9.2

(56) References Cited

U.S. PATENT DOCUMENTS

| | | | |
|---|---|---|---|
| 6,235,885 B1 | 5/2001 | Jessell et al. | |
| 6,387,656 B1 | 5/2002 | Jessell et al. | |
| 6,566,092 B1 | 5/2003 | Jessell et al. | |
| 2002/0197678 A1 | 12/2002 | Jessell et al. | |
| 2003/0104374 A1 | 6/2003 | Jessell et al. | |
| 2004/0005602 A1 | 1/2004 | Jessell et al. | |

FOREIGN PATENT DOCUMENTS

| | | | |
|---|---|---|---|
| WO | WO 95/23223 A1 | 8/1995 | |
| WO | WO 99/00516 A2 | 1/1999 | |
| WO | WO00/09676 A2 | 2/2000 | |
| WO | WO 00/18884 A1 | 4/2000 | |
| WO | WO0184933 | 11/2001 | |
| WO | WO0218545 | 3/2002 | |

OTHER PUBLICATIONS

Horner et al. Regenerating the damaged central nervous system vol. 407 pp. 963–970 2000.*
Jackowski Neural Injury repair: hope for the future as barriers to effective CNS regeneration become clearer pp. 303–317 1995.*
Hamburger, V. et al. (1951) "A Series Of Normal Stages In The Development Of The Chick Embryo" *J. Morphol.* 88:49–92 (Exhibit 1).
Langman, J. et al. (1966) "Behavior of Neuroepithelial Cells During Closure Of The Neural Tube" *J. Comp. Neur.* 127:399–411 (Exhibit 2).
Leber, S.M. et al. (1995) "Migratory Paths Of Neurons And Glia In The Embryonic Chick Spinal Cord" *J. Neurosci.* 15:1236–1248 (Exhibit 3).
Muramatsu, T. et al. (1997) "Comparison Of Three Nonviral Transfection Methods For Foreign Gene Expression In Early Chicken Embryons In Ovo" *Biochem. Biophys. Res. Commun.* 230:376–380 (Exhibit 4).

Sander, M. et al. (2000) "Ventral Neural Patterning By Nkx Homeobox Genes: Nkx6.1 Controls Somatic Motor Neuron And Ventral Interneuron Fates" *Genes & Development* 14(17):2134–2139 (Exhibit 5).
Struhl, G. et al. (1992) "Control Of Drosophila Body Pattern By The hunchback Morphogen Gradient" *Cell* 69:237–249 (Exhibit 6); and.
Yamada, T. et al. (1993) "Control Of Cell Pattern In The Neural Tube: Motor Neuron Induction By Diffusible Factors From Notochord And Floor Plate" *Cell* 73:673–686 (Exhibit 7).
Cai, J. et al. (2001) "Mice lacking the Nkx6.2 (Gtx) homeodomain transcription factor develop and reproduce normally," *Molecular and Cellular Biology* 21:4399–4403.
Palmer, T.D. et al. (1999) "Fibroblast growth factor–2 activates a latent neurogenic program in neural stem cells from diverse regions of the adult CNS," *The Journal of Neuroscience* 19: 8487–8497.
Briscoe, J. et al., (1999) "Homeobox Gene Nkx2.2 and specification of Neuronal Identity by Graded Sonic Hedgehog Signalling" *Nature* 398:622–627 (Exhibit 1).
Campbell, G. et al., (1999) "Transducing the Dpp Morphogen Gradient in the Wing of Drosophila: Regulation of Dpp Targets by brinker" *Cell* 96:553–562 (Exhibit 2).
Chiang, C. et al., (1996) "Cyclopia and Defective Axial Patterning in Mice Lacking Sonic Hedgehog Gene Function" *Nature* 383:407–413 (Exhibit 3).

(Continued)

*Primary Examiner*—Anne-Marie Falk
(74) *Attorney, Agent, or Firm*—John P. White, Esq.; Cooper & Dunham LLP

(57) ABSTRACT

Provided are genetically engineered cells comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein; which is capable of expressing homeodomain transcription factor Nkx6.1 protein and homeodomain transcription factor Irx3 protein; and which is capable of expressing homeodomain transcription factor Nkx2.2 protein or homeodomain transcription factor Nkx2.9 protein. Also provided are methods of generating such genetically engineered motor neurons, V2 neurons, and V3 neurons. Also provided are methods of treating subjects having a motor neuron injury or a motor neuron disease comprising implanting in injured/diseased neural tissue of the subject any of the provided genetically engineered cells, administering to such neural tissue retroviral expression systems which are capable of expressing the appropriate homeodomain protein(s), or transfecting neural stem cells with a retroviral vector, which is capable of expressing the required homeodomain transcription factor protein(s). Provided is a method of determining whether a chemical compound affects the generation of a motor neuron from a neural stem cell.

5 Claims, 13 Drawing Sheets

OTHER PUBLICATIONS

Dasen, J.S. et al., (1999) "Combinatorial Codes in Signaling and Synergy: Lessons From Pituitary Development" *Curr Opin. Genet. & Dev.* 9:566–574 (Exhibit 4).

Ding, Q. et al., (1998) "Diminished Sonic Hedgehog Signaling and Lack of Floor Plate Differentiation in Gli2 Mutant Mice" *Development* 125:2533–2543 (Exhibit 5).

Doetsch, F. et al., (1999) "Subventricular Zone Astrocytes Are Neural Stem Cells in the Adult Mammalian Brain" *Cell* 97:703–716 (Exhibit 6).

Ericson, J. et al., (1996) "Two Critical Periods of Sonic Hedgehog Signaling Required for the Specification of Motor Neuron Identity" *Cell* 87:661–673 (Exhibit 7).

Ericson, J. et al., (1997) "Pax6 Controls Progenitor Cell Identity and Neuronal Fate in Response to Graded Shh Signaling" *Cell* 90:169–180 (Exhibit 8).

Ericson, J. et al., (1997) "Graded Sonic Hedgehog Signaling and the Specification fo Cell Fate in the Ventral Neural Tube" *Cold Spring Harb. Symp. Quant. Biol.* 62:451–466 (Exhibit 9).

Erskine, L. et al., (1998) "Progenitor Dispersal and the Origin of Early Neuronal Phenotypes in the Chick Embryo Spinal Cord" *Dev. Biol.* 199:26–41 (Exhibit 10).

Funayama, N. et al., (1999) "Coelom Formation: Binary Decision of the Lateral Plate Mesoderm is Controlled by the Ectoderm" *Development* 126:4129–4138 (Exhibit 11).

Gage, F.H. (2000) "Mammalian Neural Stem Cells" *Science* 287:1433–1438 (Exhibit 12).

Huang, A.M. et al., (1997) "An Anteroposterior Dorsal Gradient in the Drosophila Embryo" *Genes & Dev.* 11:1963–1973 (Exhibit 13).

Ingham, P.W. (1998) "Transducing Hedgehog: The Story So Far" *EMBO J.* 17:3505–3511 (Exhibit 14).

Jazwinska, A. et al., (1999) "The Drosophila Gene brinker Reveals a Novel Mechanism of Dpp Target Gene Regulation" *Cell* 96:563–573 (Exhibit 15).

Johansson, C.B. et al., (1999) "Identification of a Neural Stem Cell in the Adult Mammalian Central Nervous System" *Cell* 96:25–34 (Exhibit 16).

Kraut, R. et al., (1991) "Spatial Regulation of the Gap Gene giant During Drosophila Development" *Development* 111:601–609 (Exhibit 17).

Krishnan, V. et al., (1997) "Mediation of Sonic Hedgehog–Induced Expression of COUP–TFII by a Protein Phosphatase" *Science* 278:1947–1950 (Exhibit 18).

Lawrence, P.A. et al., (1996) "Morphogens, Compartments, and Pattern: Lessons from Drosophila?" *Cell* 85:951–961 (Exhibit 19).

Lewis, K.E. et al., (1999) "Expression of ptc and gli Genes in talpid[3] Suggests Bifurcation in Shh Pathway" *Development* 126:2397–2407 (Exhibit 20).

Lumsden, A. et al., (1996) "Patterning the Vertebrate Neuraxis" *Science* 274:1109–1115 (Exhibit 21).

Mansouri, A. et al., (1998) "Pax3 and Pax7 are Expressed in Commissural Neurons and Restrict Ventral Neuronal Identity in the Spinal Cord" *Mech. Dev.* 78:171–178 (Exhibit 22).

Marti, E. et al., (1995) "Distribution of Sonic Hedgehog Peptides in the Developing Chick and Mouse Embryo" *Development* 121:2537–2547 (Exhibit 23).

Matise, M.P. et al., (1998) "Gli2 is Required for Induction of Floor Plate and Adjacent Cells, But Not Most Ventral Neurons in the Mouse Central Nervous System" *Development* 125:2759–2770 (Exhibit 24).

McDowell, N. et al., (1999) "Activin as a Morphogen in Xenopus Mesoderm Induction" *Semin. Cell & Dev. Biol.* 10:311–317 (Exhibit 25).

Minami, M. et al., (1999) "Brinker is a Target of Dpp in Drosophila that Negatively Regulates Dpp–dependent Genes" *Nature* 398:242–246 (Exhibit 26).

Pabst, O. et al., (1998) "Nkx–9 is a Novel Homeobox Transcription Factor Which Demarcates Ventral Domains in the Developing Mouse CNS" *Mech. Dev.* 73:85–93 (Exhibit 27).

Papin, C. et al., "Gradual Refinement fo Activin–Induced Thresholds Requires Protein Synthesis" *Dev. Biol.* 217:166–172 (Exhibit 28).

Pierani, A. et al., (1999) "A Sonic Hedgehog–Independent, Retinoid–Activated Pathway of Neurogenesis in the Ventral Spinal Cord" *Cell* 97:903–915 (Exhibit 29).

Qiu, M. et al., (1998) "Control of Anteroposterior and Dorsoventral Domains of Nkx–6.1 Gene Expression Relative to Other Nkx Genes During Vertebrate CNS Development" *Mech. Develop.* 72:77–88 (Exhibit 30).

Roelink, H. et al., (1995) "Floor Plate and Motor Neuron Induction by Different Concentrations of the Amino–Terminal Cleavage Product of Sonic Hedgehog Autoproteolysis" *Cell* 81:445–455 (Exhibit 31).

Rowitch, D. H. et al., (1999) "Sonic hedgehog Regulates Proliferation and Inhibits Differentiation of CNS Precursor Cells" *J. Neurosci.* 19:8954–8965 (Exhibit 32).

Ruiz i Altaba, A. (1999) "Gli Proteins and Hedgehog Signaling: Development and Cancer" *Trends Genet.* 15:418–425 (Exhibit 33).

Sharma, K. et al., (1998) "LIM Homeodomains Factors Lhx3 and Lhx4 Assign Subtype Identities for Motor Neurons" *Cell* 95:817–828 (Exhibit 34).

Smith, J.C. (1995) "Mesoderm–Inducing Factors and Mesodermal Patterning" *Curr. Opin. Cell Biol.* 7:856–861 (Exhibit 35).

Tanabe, Y. et al., (1998) "Specification of Motor Neuron Identity by the MNR2 Homeodomain Protein" *Cell* 95:67–80 (Exhibit 36).

Wu, X. et al., (1998) "Two Distinct Mechanisms for Differential Positioning of Gene Expression Borders Involving the Drosophila Gap Protein Giant" *Development* 125:3765–3774 (Exhibit 37).

U.S. Appl. No. 09/654,462, filed Sep. 1, 2000 on behalf of Thomas M. Jessell et al., including allowed claims (Exhibit 1).

U.S. Appl No. 10/362,437, filed Feb. 20, 2003 on behalf of Thomas M. Jessell et al. (Exhibit 2).

Anderson, S.A. et al., (1997) "Interneuron Migration from Basal Forebrain to Neocortex: Dependence on DLx Genes", *Science* 278:474–476 (Exhibit 5).

Arber, S. et al., (1999) "Requirement for the Homeobox Gene Hb9 in the Consolidation of Motor Neuron Identity", *Neuron* 23:659–674 (Exhibit 6).

Briscoc, J. et al., (2000) "A Homeodomain Protein Code Specifies Progenitor Cell Identity and Neuronal Fate in the Ventral Neural Tube", *Cell* 101:435–445 (Exhibit 7).

Burrill, J.D. et al., (1997) "PAX2 is expressed in multiple spinal cord interneurons, including a population on EN1[+] interneurons that require PAX6 for their development", *Development* 124:4493–4503 (Exhibit 8).

Chu, H. et al., (1998) "Formation and specification of ventral neuroblasts is controlled by vnd in Drosophila neurogenesis", *Genes & Dev.* 12:3613–3624 (Exhibit 9).

Goulding, M.D. et al., (1991) "Pax–3, a novel murine DNA binding protein expressed during early neurogenesis", *EMBO J.* 10:1135–47 (Exhibit 10).

Hammerschmidt, M. et al., (1997) "The world according to hedgehog", *Trends Genet* 13:14–21 (Exhibit 11).

Hebrok, M. et al., (1998) "Notochord repression of endodermal Sonic hedgehog permits pancreas development", *Genes & Dev.* 12: 1705–1713 (Exhibit 12).

Inoue, H. et al., (1997) "Isolation, characterization, and chromosomal mapping of the human Nkx6.1 gene (NKX6A), a new pancreatic islet homeobox gene", *Genomics* 40:367–370 (Exhibit 13).

Matise, M.P. et al., (1997) "Expression Patterns of Development Control Genes in Normal and Engrailed–1 Mutant Mouse Spinal Cord Reveal Early Diversity in Developing Interneurons", *J. Neurosci.* 17:7805–7816 (Exhibit 14).

McDonald, J. A. et al., (1998) "Dorsoventral patterning in the Drosophila central nervous system: the vnd homeobox gene specifies ventral column identity", *Genes & Dev.* 12:3603–3612 (Exhibit 15).

Pattyn, A. et al., (1997) "Expression and interactions of the two closely related homeobox genes Phox2a and Phox2b during neurogensis", *Development* 124:4065–4075 (Exhibit 16).

Rubenstein, J.L. et al., (1998) "Patterning of the embryonic forebrain", *Curr. Opin. Neurobiol.* 8:18–26 (Exhibit 17).

Rubenstein, J.L. et al., (1998) "Regionalization of the Prosencephalic Neural Plate", *Annu. Rev. Neurosci.* 21:445–477 (Exhibit 18).

Sussel, L. et al., (1999) "Loss of Nkx2.1 homeobox gene function results in a ventral to dorsal molecular respecification within the basal telencephalon: evidence for a transformation of the pallidium into the striatum", *Development* 126:3359–3370 (Exhibit 19).

Tanabe, Y. et al., (1996) "Diversity and Pattern in the Developing Spinal Cord", *Science* 274:1115–23 (Exhibit 20).

Thaler, J. et al., (1999) "Active Suppression of Interneuron Programs within Developing Motor Neurons Revealed by Analysis of Homeodomain Factor HB9", *Neuron* 23:675–687 (Exhibit 21).

Tsuchida, T. et al., (1994) "Topographic Organization of Embryonic Motor Neurons Defined by Expression of LIM Homeobox Genes", *Cell* 79:957–970 (Exhibit 22).

Valerius, M. T. et al., (1995) "Gsh–1: A Novel Murine Homeobox Gene Expressed in the Central Nervous System", *Dev. Dyn.* 203:337–51 (Exhibit 23).

Weiss, J. B. et al., (1998) "Dorsoventral patterning in the Drosophila central nervous system: the intermediate neuroblasts defective homeobox gene specifies intermediate column identity", *Genes & Dev.* 12:3591–3602 (Exhibit 24).

Mirmira et al. (2000) "Beta–Cell Differentiation Factor Nkx6.1 Contains Distinct DNA Binding Interference And Transcriptional Repression Domains", *J. Biol. Chem.* 275(19):1473–14751 (Exhibit 25).

Oster et al. (1998) "Homeobox Gene Product Nkx 6.1 Immunoreactivity In Nuclei Of Endocrine Cells Of Rat And Mouse Stomach", *J. Histochem. And Cytochem.* 46(6):717–721 (Exhibit 26).

Schwitzgebel et al. (2000) "Expression Of Neurogenin3 Reveals An Islet Cell Precursor Population In the Pancreas", *Genes & Development* 127:3533–3542 (Exhibit 27).

Friedman, T. (Jun. 1997) "Overcoming The Obstacles To Gene Therapy", *Scientific American*, pp. 96–101 (Exhibit 28).

Orkins, S.H. and Motulsky, A.G. (1995) "Report And Recommendations Of The Panel To Assess The NIH Investment In Research On Gene Therapy" (Exhibit 29).

Verma, I.M. and Somia, N. (1997) "Gene Therapy—Promises, Problems and Prospects", *Nature* 389: 239–242 (Exhibit 30).

"Stem Cells: Scientific Progress and Future Research Directions" (Jun. 2001) Department of Health and Human Services, pp. 1–9 (Exhibit 31).

Basler, K. et al. (1993) "Control of cell pattern in the neural tube: Regulation of cell differentiation by dorsalin–1, a novel TGF beta family member", *Cell* 73: 687–702.

Briscoc, J., and Ericson, J. (2001) "Specification of neuronal fates in the ventral neural tube", *Curr Opin Neurobiol* 1:43–49.

Briscoe, J. et al. (2001) "A hedgehog–insensitive form of patched provides evidence for direct long–range morphogen activity of Sonic hedgehog in the neural tube", *Molecular Cell* 7: 1279–1291.

Cai, J. et al. (1999) "Expression and regulation of the chicken Nkx–6.2 homeobox gene suggest its possible involvement in the ventral neural patterning and cell fate specification" *Dev Dyn* 216:459–468.

Davis, C.A. et al. (1991) "Examining pattern formation in mouse, chicken and frog embryos with an En–specific antiserum" *Development* 111:287–298.

Eberhard, D. et al. (2000) "Transcriptional repression by Pax5 (BSAP) through interaction with corepressors of the Groucho family" *EMBO J.* 19:2292–2303.

Hoshiyama, D. et al. (1998) "Sponge Pax cDNA related to PAX–2/5/8 and ancient gene duplications in the Pax family" *J. Mol. Evol.* 47: 640–648.

Jörgensen, M.C. et al. (1999) "Cloning and DNA–binding properties of the rat pancreatic beta–cell–specific factor Nkx6.1" *FEBS Lett.* 461: 287–294.

Kraut, R. and Levine, M. (1991) "Mutually repressive interactions between the gap genes giant and Kruppel define middle body regions of the Drosophila embryo", *Development* 111:611–621.

Komuro, I. et al. (1993) "Gtx: a novel murine homeobox–containing gene, expressed specifically in glial cells of the brain and germ cells of testis, has a transcriptional repressor activity in vitro for a serum–inducible promoter" *EMBO* 12: 1387–1401.

Lee, S. et al. (2001) "Cloning, expression and chromosomal location of NKX6B to 10q26, a region frequently deleted in brain tumors" *Mammalian Genome* 12: 157–162.

Moran–Rivard, L. et al. (2001) "Evxl is a postmitotic determinant of V0 interneuron identity in the spinal cord" *Neuron* 29: 385–399.

Mombaerts, P. et al. (1996) "Visualizing an olfactory sensory map" *Cell* 87: 675–686.

Muhr, J. et al. (2001) "Groucho–mediated transcriptional repression establishes progenitor cell pattern and neuronal fate in the ventral neural tube" *Cell* 104: 861–873.

Novitch, B. et al. (2001) "Coordinate regulation of motor neuron subtype identity and pan–neural properties by the bHLH repressor Olig2", *Neuron* 31(5): 773–789.

Nutt, S.L. et al. (1999) "Commitment to the B–lymphoid lineage depends on the transcription factor Pax5" *Nature* 401: 556–562.

Pabst, O. et al. (2000) "NKX2 gene expression in neuroectoderm but not in mesendodermally derived structures depends on sonic hedgehog in mouse embryos" *Dev Genes Evol* 210: 47–50.

Peters, T. et al. (2001) "Organization of mouse Iroquois homeobox genes in two clusters suggests a conserved regulation and function in vertebrate development" *Genome Res.* 10:1453–62.

Pierani, A. et al. (2001) "Control of interneuron fate in the developing spinal cord by the progenitor homeodomain protein Dbx1" *Neuron* 29: 367–384.

Rolink, A.G. et al. (1999) "Long–term in vivo reconstitution of T–cell development by Pax5–deficient B–cell progenitors" *Nature* 401: 603–606.

Schaeren–Wiemers, N. and Gerfin–Moser, A. (1993) "A single protocol to detect transcripts of various types and expression levels in neural tissue and cultured cells: in situ hybridization using digoxigenin–labeld cRNA probes" *Histochemistry* 100: 431–440.

Shoji, H. et al. (1996) "Regionalized expression of the Dbx family homeobox genes in the embryonic CNS of the mouse" *Mech. Dev.* 56: 25–39.

Stanojevic, D., Small, S. and Levine, M. (1991) "Regulation of a segmentation stripe by overlapping activators and repressors in the Drosophila embryo" *Science* 254: 1385–1387.

Tanaka, M., Yamasaki, N., Izumo, S. (2000) "Phenotypic characterization of the murine Nkx2.6 homeobox gene by gene targeting" *Mol Cell Biol.* 8: 2874–2879.

Toresson, H., Potter, S.S. and Campbell, K. (2000) "Genetic control of dorsal–ventral identity in the telencephalon: opposing roles for Pax6 and Gsh2" *Development* 127: 4361–4371.

Wang, C.C. et al. (2000) "Conserved linkage of NK–2–1/2–9 in mammals" *Mamm. Genome* 11: 466–468.

Yun, K., Potter, S. and Rubenstein, J.L. (2001) "Gsh2 and Pax6 play complementary roles in dorsoventral patterning of the mammalian telencephalon" *Development* 128: 193–205.

* cited by examiner

HOMEODOMAIN PROTEIN CODE SPECIFYING PROGENITOR CELL IDENTIFY AND NEURONAL FATE IN THE VENTRAL NEURAL TUBE

The invention disclosed was herein made in the course of work under NIH Grant No. RO1 NF33245-07. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

In many developing tissues, the generation of distinct cell types is initiated by the action of extracellular signals provided by local organizing centers. Certain signals have the additional feature of directing distinct cell fates at different threshold concentrations, and thus function as morphogens (Wolpert, 1969). In Drosophila, the patterning of embryonic segments and imaginal discs involves the graded signaling activities of the Hedgehog, Wingless and TGFβ-related proteins (Lawrence and Struhl, 1996). In vertebrate embryos the specification of mesodermal cell types has similarly been suggested to depend on the graded signaling activity of members of the TGFβ family (Smith, 1995; McDowell and Gurdon, 1999). The generation of cell pattern through morphogen signaling demands an effective means of converting graded extracellular activities into all-or-none distinctions in cell fate. But the mechanisms used to achieve such conversions have been poorly defined, particularly in vertebrate tissues.

In the developing vertebrate nervous system, Sonic hedgehog (Shh) appears to function as a gradient signal. The secretion of Shh by the notochord and floor plate controls the specification of ventral cell types (Marti et al., 1995; Roelink et al., 1995; Chiang et al., 1996; Ericson et al., 1996). Five distinct classes of ventral neurons can be generated in vitro in response to progressive two-to-three fold changes in extracellular Shh concentration (Ericson et al., 1997a, b). Moreover, the position at which each of these neuronal classes is generated in vivo is predicted by the concentration of Shh required for their induction in vitro: neurons generated in progressively more ventral regions of the neural tube require correspondingly higher concentrations of Shh for their induction (Ericson et al., 1997a). These observations have led to the view that the position that ventral progenitor cells occupy within a ventral-to-dorsal gradient of extracellular Shh activity directs their differentiation into specific neuronal subtypes (Ericson et al., 1997b).

In turn, these findings have focused attention on the steps by which graded Shh signaling directs the diversification of neural progenitor cells. Several homeodomain proteins, Pax7, Pax3, Pax6, Dbx1, Dbx2 and Nkx2.2, are expressed by ventral progenitor cells and their expression is regulated by Shh signaling (Goulding et al., 1993; Ericson et al., 1996; Ericson et al., 1997a; Briscoe et al., 1999; Pierani et al., 1999). Moreover, the pattern of generation of certain ventral neuronal subtypes is perturbed in mice carrying mutations in these Pax genes and in the Nkx2.2 gene (Ericson et al., 1997a; Mansouri and Gruss, 1998; (Briscoe et al., 1999), supporting the view that homeodomain proteins expressed by ventral progenitor cells regulate neuronal subtype identity. However, two important aspects of the link between Shh signaling and neuronal identity remain obscure. First, it is unclear how the presumed extracellular gradient of Shh activity results in stable and sharply delineated domains of homeodomain protein expression within ventral progenitor cells. Second, the spatial information provided by the homeodomain proteins characterized to date is insufficient to explain the diversity of neuronal subtypes generated at different dorsoventral positions.

In the first series of experiments these two issues are addressed. It is show first that the homeodomain proteins Nkx6.1 and Irx3 are expressed by progenitor cells in discrete domains of the ventral neural tube and are regulated by graded Shh signaling. The differential expression of five class I (Shh-repressed) proteins, Pax7, Irx3, Dbx1, Dbx2 and Pax6, and two class II (Shh-induced) proteins, Nkx6.1 and Nkx2.2, subdivides the ventral neural tube into five cardinal progenitor domains. Misexpression of individual proteins in the neural tube in vivo in these experiments provides evidence that cross-repressive interactions between class I and class II proteins establish individual progenitor domains and maintain their sharp boundaries, suggesting a mechanism by which graded Shh signals are converted into all-or-none distinctions in progenitor cell identity. In addition, the experiments show that the spatial patterns of expression of Nkx6.1, Irx3 and Nkx2.2 are sufficient to direct both the position and fate of three neuronal subtypes generated in ventral third of the neural tube. These findings suggest a model of ventral neuronal patterning that may provide insight into how extracellular signals are interpreted during the patterning of other vertebrate tissues.

Distinct classes of neurons are generated at defined positions in the ventral neural tube in response to a gradient of Sonic Hedgehog (Shh) activity. A set of homeodomain transcription factors expressed by neural progenitors act as intermediaries in Shh-dependent neural patterning. These homeodomain factors fall into two classes: class I proteins are repressed by Shh and class II proteins require Shh signaling for their expression. The profile of class I and class II protein expression defines five progenitor domains, each of which generates a distinct class of post-mitotic neurons. Cross-repressive interactions between class I and class II proteins appear to refine and maintain these progenitor domains. The combinatorial expression of three of these proteins—Nkx6.1, Nkx2.2 and Irx3—specifies the identity of three classes of neurons generated in the ventral third of the neural tube.

Sonic hedgehog (Shh) signaling has a critical role in the control of neuronal fate in the ventral half of the vertebrate central nervous system (CNS). The genetic programs activated in Shh-responsive progenitor cells, however, remain poorly defined. To test whether members of the Nkx class of homeobox genes have a prominent role in the specification of ventral cell types the second series of experiments examined patterns of neurogenesis in mice carrying a targeted mutation in the Nkx class homeobox gene Nkx6.1. In Nkx6.1 mutants there is a dorsal-to-ventral switch in the identity of progenitor cells and in the fate of post-mitotic neurons. At many axial levels there is a complete block in the generation of V2 interneurons and motor neurons and a compensatory ventral expansion in the domain of generation of V1 neurons. These studies support the idea that an Nkx gene code controls regional pattern and neuronal fate in the ventral region of the mammalian CNS.

SUMMARY OF THE INVENTION

This invention provides a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein.

This invention provides a method of generating a genetically engineered motor neuron which is capable of expressing homeodomain transcription factor Nkx6.1 protein but does not express homeodomain transcription factor Irx3 protein or homeodomain transcription factor Nkx2.2 protein which comprises treating a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein under conditions such that the retroviral expression system expresses homeodomain transcription factor Nkx6.1 protein so as to thereby generate the genetically engineered motor neuron.

This invention also provides a genetically engineered cell comprising a neural stem cell and retroviral expression system in the neural stem cell, which is capable of expressing homeodomain transcription factor Nkx6.1 protein and homeodomain transcription factor Irx3 protein.

This invention further provides a method of generating a genetically engineered V2 neuron which is capable of expressing homeodomain transcription factor Nkx6.1 protein and homeodomain transcription factor Irx3 protein which comprises treating a genetically engineered cell comprising a neural stem cell and retroviral expression system in the neural stem cell, which is capable of expressing homeodomain transcription factor Nkx6.1 protein and homeodomain transcription factor Irx3 protein, under conditions such that the retroviral expression system expresses homeodomain transcription factor Nkx6.1 protein and homeodomain transcription factor Irx3 protein so as to thereby generate the genetically engineered V2 neuron.

This invention provides a genetically engineered cell comprising a neural stem cell and retroviral expression system in the neural stem cell, which is capable of expressing homeodomain transcription factor Nkx.2.2 protein or homeodomain transcription factor Nkx2.9 protein.

This invention also provides a method of generating a genetically engineered V3 neuron which is capable of expressing homeodomain transcription factor Nkx.2.2 protein or homeodomain transcription factor Nkx2.9 protein which comprises treating a genetically engineered cell comprising a neural stem cell and retroviral expression system in the neural stem cell, which is capable of expressing homeodomain transcription factor Nkx.2.2 protein or homeodomain transcription factor Nkx2.9 protein, under conditions such that the retroviral expression system expresses homeodomain transcription factor Nkx.2.2 protein or homeodomain transcription factor Nkx2.9 protein so as to thereby generate the genetically engineered V3 neuron.

This invention further provides a method of treating a subject having a motor neuron injury or a motor neuron disease comprising: implanting in injured or diseased neural tissue of the subject a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein.

This invention still further provides a method of treating a subject having a motor neuron injury or a motor neuron disease comprising: administering to injured or diseased neural tissue of adult spinal cord a retroviral expression system, which is capable of expressing homeodomain transcription factor Nkx6.1 protein but does not express homeodomain transcription factor Irx3 protein or homeodomain transcription factor Nkx2.2 protein.

This invention provides a method of treating subject having a motor neuron injury or a motor neuron disease comprising: (a) transfecting neural stem cells with a retroviral vector, which is capable of expressing homeodomain transcription factor Nkx6.1 protein but does not express homeodomain transcription factor Irx3 protein or homeodomain transcription factor Nkx2.2 protein; and (b) injecting the transfected neural stem cells of step (a) into the central canal of the spinal cord under conditions which allow the injected transfected neural stem cells to be incorporated into the ependimal layer of the spinal cord.

This invention provides a method of determining whether a chemical compound affects the generation of a motor neuron from a neural stem cell which comprises: a) contacting a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein with the chemical compound under conditions such that in the absence of the compound the neural stem cell expresses homeodomain transcription factor Nkx6.1 protein and generates a motor neuron; and b) determining what effect, if any, the compound has on generation of the motor neuron.

BRIEF DESCRIPTION OF THE FIGURES

(FIG. 1B) The combinatorial expression of class I and class II proteins defines five ventral progenitor domains. Images show protein expression in the neural tube of HH stage 22 chick embryos.

(FIG. 2A) Repression of class I gene expression by Shh. Expression of Pax7 and Irx3 in [i] explants grown for 24 h alone or in the presence Shh-N. Repression of Pax7 requires ~1 nM Shh-N (Ericson et al., 1996) whereas repression of Irx3 requires ~3 nM Shh-N. Images representative of 12 explants.

(FIG. 2B) Shh induces class II proteins. Expression of Nkx2.2 and Nkx6.1 in [i] explants exposed to Shh-N for 24 h. Nkx2.2 expression requires ~4 nM Shh-N whereas Nkx6.1 expression requires ~0.25 nM Shh-N. Images representative of 12 explants.

(FIG. 2C) Expression of class II proteins requires Shh signaling at stage 10 but not at stage 15. [vf] explants taken from HH stages 10 or 15 embryos grown in the presence of anti-Shh IgG and analyzed for the expression of Nkx2.2, Nkx6.1 and Shh at 24 h. Stage 10 [vf]

explants grown alone express Nkx2.2 and Nkx6.1. Exposure of stage 10 [vf] explants to anti-Shh IgG blocks the expression of Nkx2.2 and Nkx6.1. Nkx6.1 expression continues in the floorplate of [vf] explants grown in the presence of anti-Shh IgG. Stage 15 [vf] explants grown alone or with anti-Shh IgG express Nkx2.2 and Nkx6.1 in similar domains. The slight narrowing of the domain of Nkx2.2 expression could reflect an influence of Shh on cell proliferation. Anti-Shh IgG blocks Shh signaling effectively in stage 15 [vf] explants (data not shown; see Briscoe et al., 1999). Images representative of 12 explants.

Figure 3:
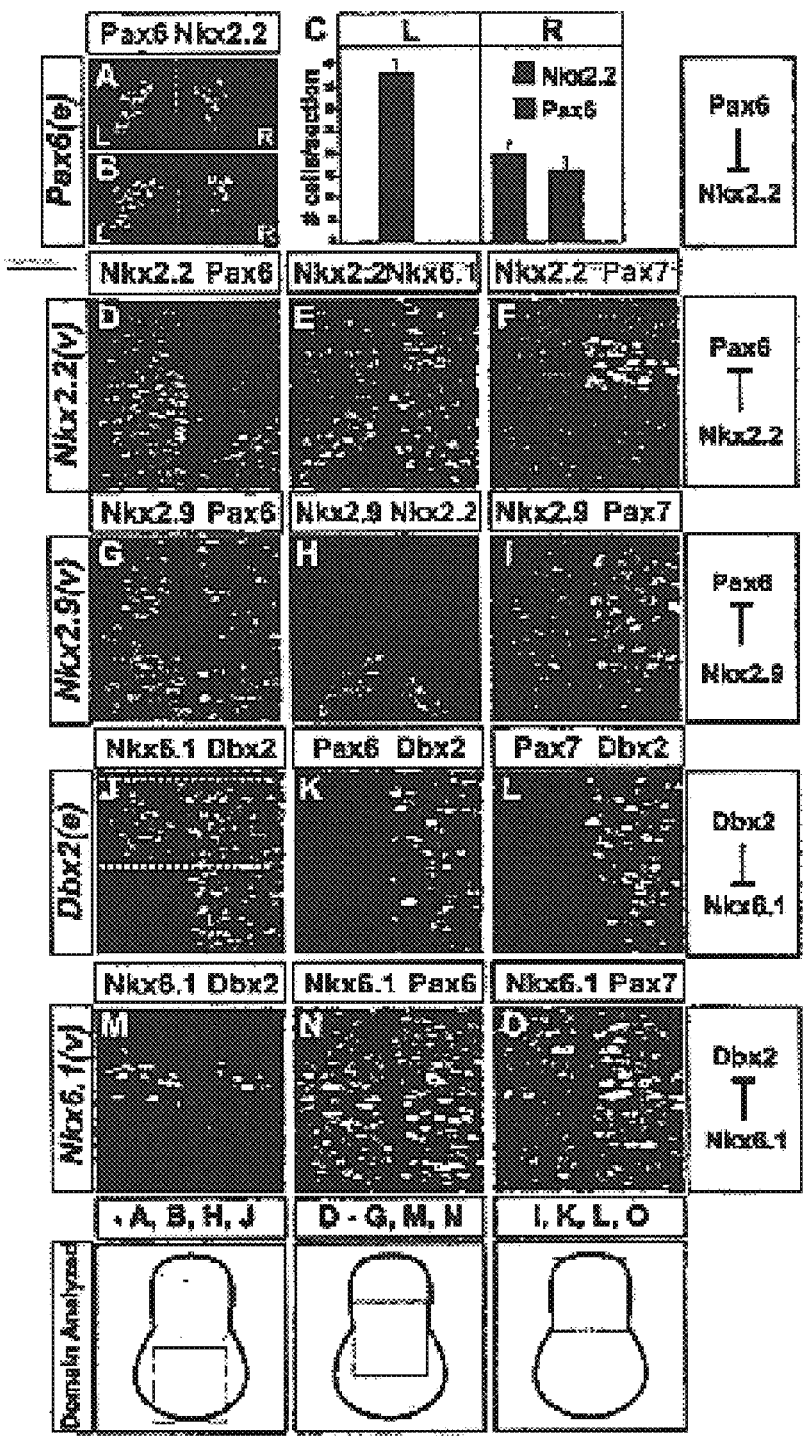

FIGS. 3A–3O. Repressive Interactions at the pMN/p3 and p1/p2 Boundaries.

Pax6, Nkx2.2, Nkx2.9, Dbx2 and Nkx6.1 were ectopically expressed using in ovo electroporation (e) or retroviral transduction (v) and the pattern of expression of other progenitor homeodomain proteins was analyzed at HH stages 22–24. (FIGS. 3A, 3B) Ectopic expression of Pax6 in the p3 domain results in the cell-autonomous repression of Nkx2.2 A similar level of expression of Pax6 does not repress Dbx2 (data not shown). (FIG. 3C) Number of Pax6$^+$ and Nkx2.2$^+$ cells within the p3 domain of untransfected (left; L) and transfected (right; R) halves of the neural tube (mean±s.e.m; n=5). (FIGS. 3D–3F) Misexpression of Nkx2.2 dorsal to the p3 domain results in the cell-autonomous downregulation of Pax6 (FIG. 3D). Neither Nkx6.1 (FIG. 3E) or Pax7 (FIG. 3F) are repressed by ectopic Nkx2.2 expression. Images representative of 10 embryos. Similar results were obtained after misexpression of Nkx2.2 by electroporation (not shown). (FIGS. 3G–3J) Ectopic expression of Nkx2.9 represses Pax6 expression in a cell-autonomous manner (FIG. 3G). Nkx2.9 does not induce Nkx2.2 expression (FIG. 3H). Nkx2.9 does not repress Pax7 expression (FIG. 3I). Images representative of 10 embryos. (FIG. 3J) Ectopic ventral expression of Dbx2 results in the cell-autonomous repression of Nkx6.1. Ectopic expression of Dbx2 does not repress Pax6 (FIG. 3K) or Pax7 (FIG. 3L). (FIGS. 3M–3O) Misexpression of Nkx6.1 dorsal to the p2 domain represses Dbx2 (FIG. 3M) but not Pax6 (FIG. 3N) or Pax7 (FIG. 3O) expression. Images representative of 10 embryos.

FIGS. 4A–4L Each Progenitor Domain Generates a Distinct Neuronal Subtype.

Figure 4:
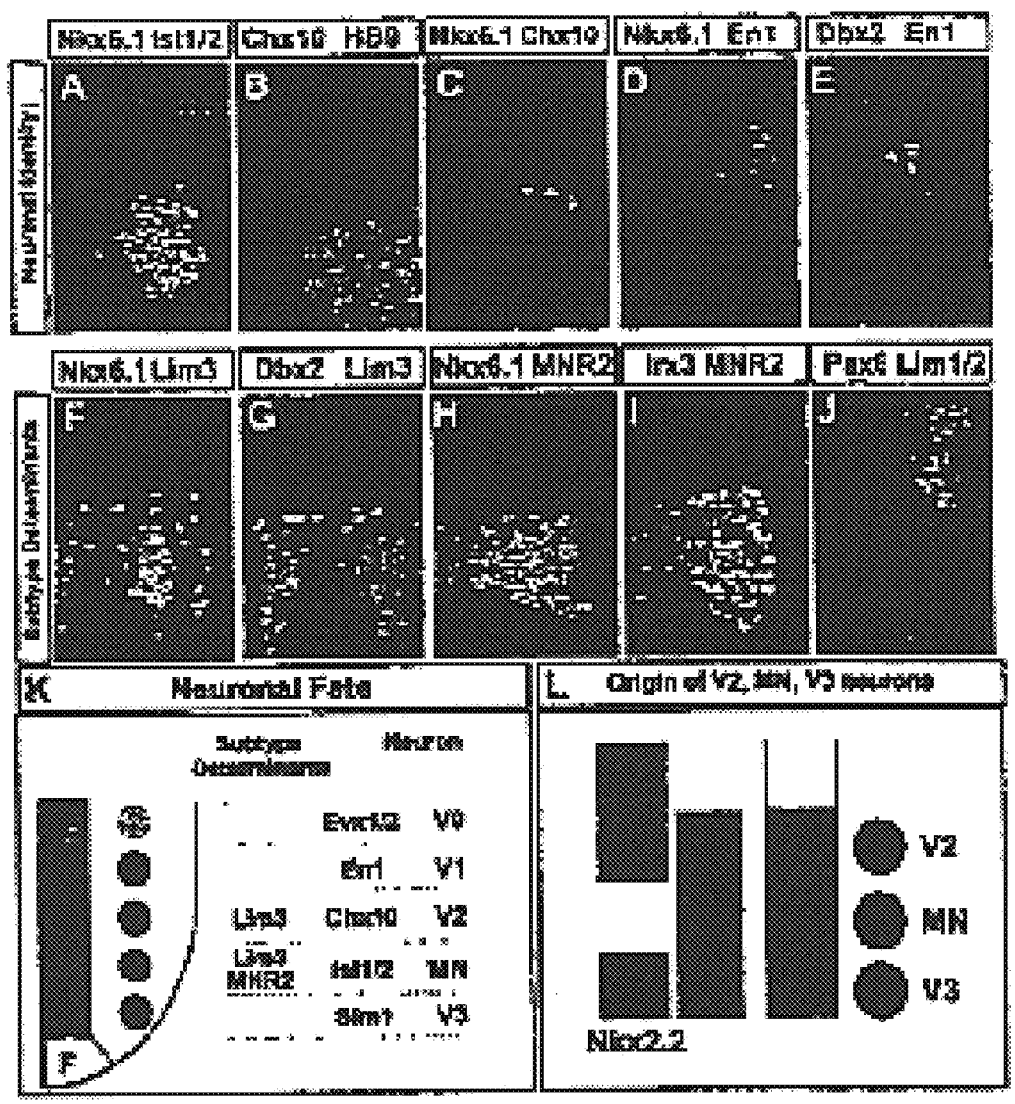

(FIGS. 4A–4E) Relationship between class I and class II proteins and neuronal markers. The domain of Nkx6.1 expression encompasses Isl1/2 MNs (FIG. 4A) and Chx10 V2 neurons (FIG. 4C) but is positioned ventral to En1 V1 neurons (FIG. 4D). Chx10 V2 neurons are generated dorsal to HB9 MNs (FIG. 4B). En1 V1 neurons are generated at the ventral extent of the Dbx2 domain (FIG. 4E). Images from HH stage 22–24 embryos. (FIGS. 4F–4J) Relationship between class I and class II proteins and neuronal subtype determinants. The domain of Nkx6.1 expression encompasses the domain of generation of Lim3 (FIG. 4F) and MNR2 cells (FIG. 4H). Lim3 cells are positioned ventral to the domain of Dbx2 expression (FIG. 4G). MNR2 cells are positioned ventral to the domain of Irx3 expression (FIG. 4I). Lim1/2 cells derive from Pax6 progenitors (FIG. 4J). (FIG. 4K) The relationship between progenitor domain identity and neuronal fate. (FIG. 4L) The progenitor homeodomain code within the three ventral-most domains of neurogenesis.

Figure 5:
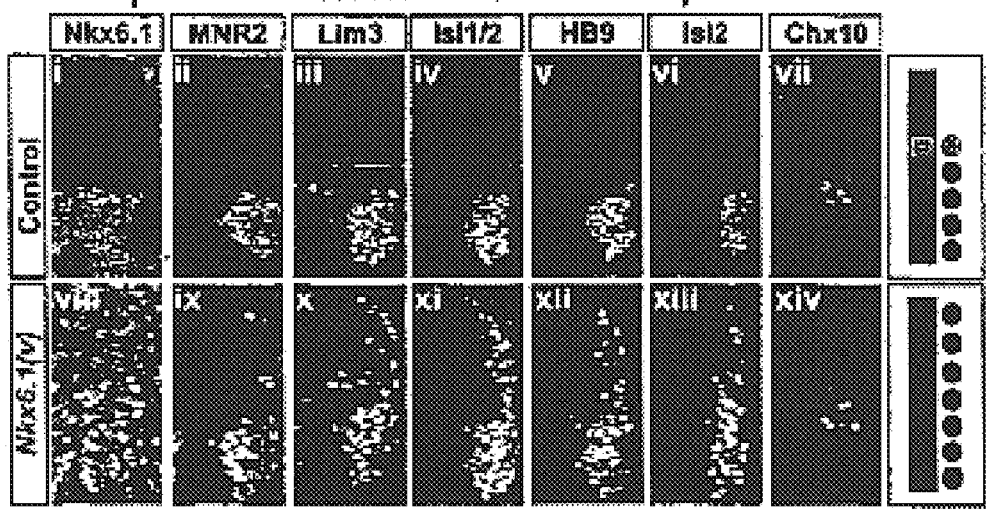
Figure 5:
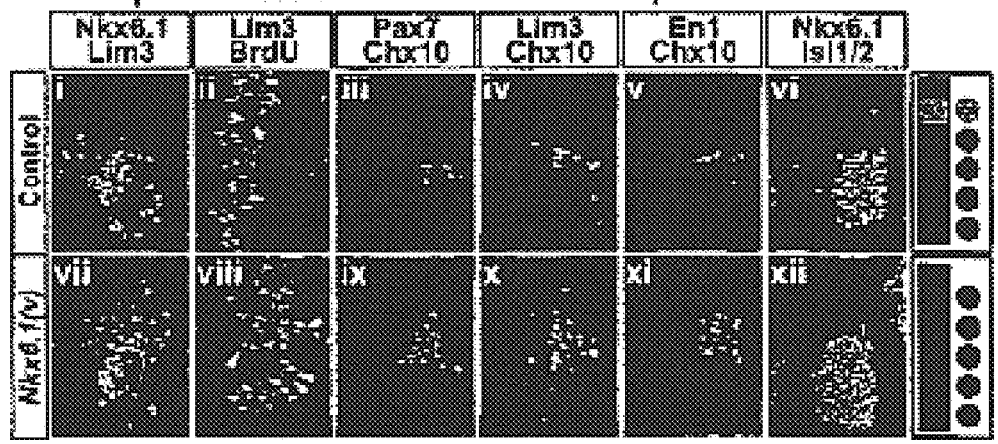
Figure 5:
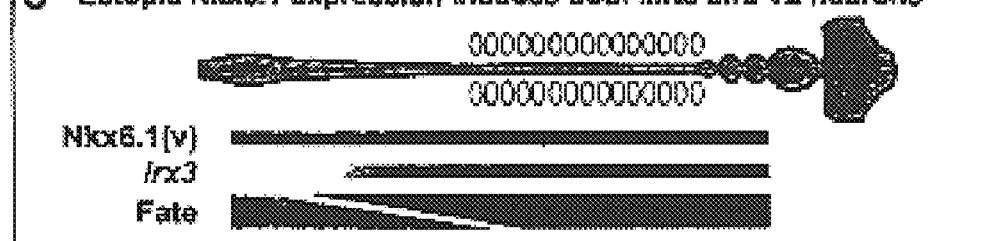

FIGS. 5A–5C Nkx6.1 Induces both Motor Neurons and V2 Neurons.

Patterns of protein expression obtained after misexpression of Nkx6.1 at rostral (FIG. 5A) and caudal (FIG. 5B) levels of retrovirally-infected embryos. (FIG. 5A) At caudal (lumbar) regions, misexpression of Nkx6.1 results in ectopic dorsal expression of MNR2 (ii and ix), Lim3 (iii and x), Isl1 (iv and xi), HB9 (v and xii) and Isl2 (vi and xiii). Misexpression of Nkx6.1 induces ectopic Chx10 expression at low incidence and only within the p0 and p1 domain (vii and xiv and data not shown). Electroporation of stage 10 embryos with Nkx6.1 results in ectopic MNs, at both rostral and caudal levels of the spinal cord (data not shown). (FIG. 5B) In rostral (cervical/thoracic) regions of infected embryos, misexpression of Nkx6.1 results in the ectopic induction of V2 neurons. Ectopic expression of Chx10 (ix, x, and xi) and Lim3 (vii, viii, x, and xi) is detected ventral to the boundary of Pax7 expression (ix) in the p1 and p0 domains. The misexpression of Nkx6.1 decreases the number of En1 V1 neurons (xi) and Evx1 V0 neurons (data not shown), but does not induce MNs (xii). Many ectopic Lim3 cells are labeled by a 30 min BrdU pulse, indicating that Nkx6.1 induces Lim3 expression in progenitor cells. Images representative of 10 experiments. (FIG. 5C) The relationship between the domains of ectopic dorsal Nkx6.1 expression, the pattern of expression of Irx3 at the time of onset of ectopic Nkx6.1 expression, and the fate of neurons that emerge from the domain of ectopic Nkx6.1 expression.

FIGS. 6A–6F Irx3 Represses Motor Neuron Generation and Induces V2 Neurons.

Figure 6:
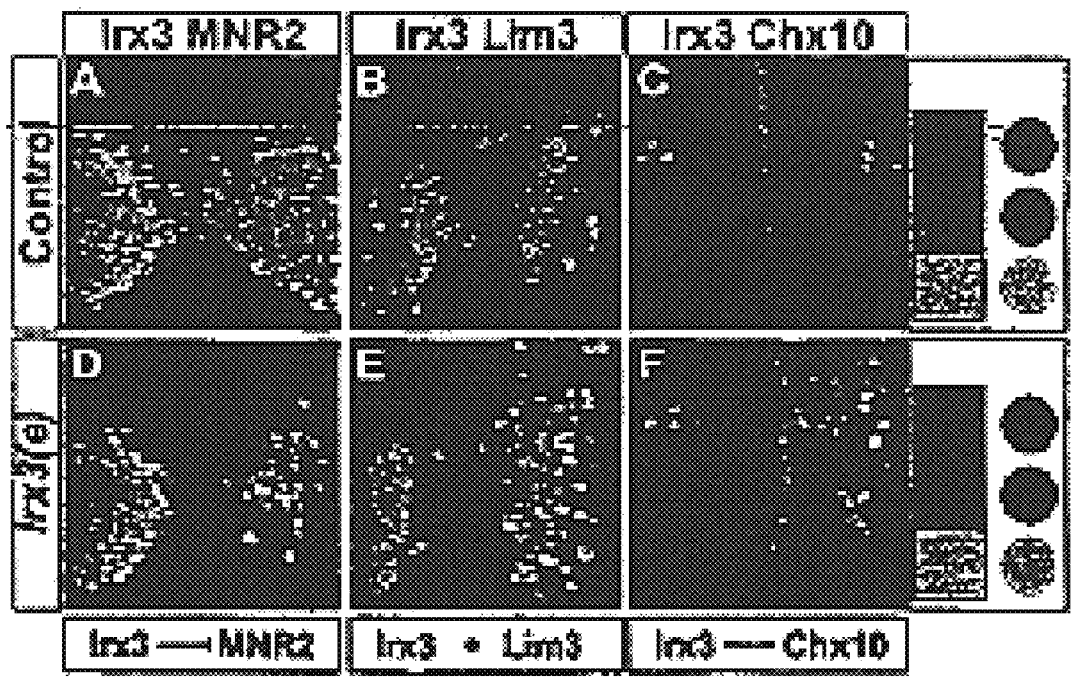

(FIG. 6A) The ventral limit of Irx3 expression corresponds to the dorsal extent of MNR2$^+$ cells in control embryos. Progenitor cells in the ventral-most domain of Irx3 expression give rise to V2 neurons that express Lim3 (FIG. 6B) and Chx10 (FIG. 6C). After ventral misexpression of Irx3 by electroporation there is no change in the pattern of Lim3 expression (FIG. 6E) but MNR2$^+$ cells are repressed (FIG. 6D) and Chx10$^+$ V2 neurons are generated within the pMN domain (FIG. 6F). Images representative of 10 experiments.

Figure 7:
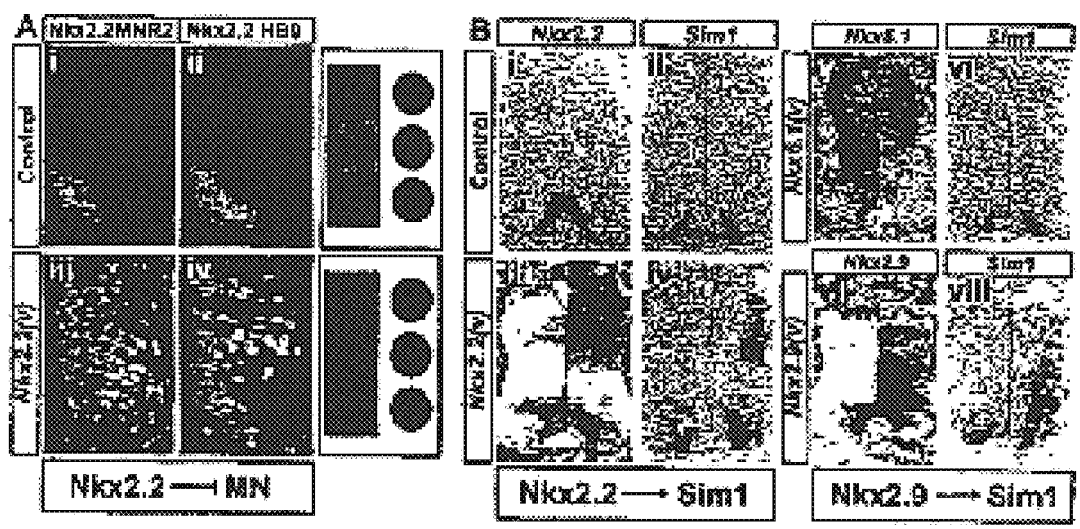

FIGS. 7A–7B Nkx2.2 Activity Represses Motor Neuron Generation and Induces V3 Neurons.

(FIG. 7A) MNR2$^+$ MN progenitors (i) and HB9$^+$ MNs (ii) are not generated from Nkx2.2 progenitors in control embryos (i and ii). Ectopic expression of Nkx2.2 (iii and iv) in pMN progenitors represses MNR2 (iii) and HB9 (iv) expression. Some more lateral cells coexpress Nkx2.2 and MN markers, probably because cells were infected with Nkx2.2 virus after they had committed to a MN fate. (FIG. 7B) Sim1$^+$ V3 neurons (ii) are generated from Nkx2.2 progenitors (i) in the p3 domain of control embryos. Misexpression of Nkx2.2 (iii) results in the ectopic dorsal expression of Sim1 (iv). Nkx6.1 (v) has no effect on Sim1 expression (vi). Nkx2.9 (vii) is sufficient to induce V3 neurons (viii). Images representative of 10 experiments.

FIGS. 8A–8C Three Phases of Ventral Neural Patterning.

(FIG. 8A) Graded Shh signaling initiates dorsoventral restrictions in the domains of class I and class II protein expression within the ventral neural tube. Class I proteins are repressed by Shh signals and class II proteins requires Shh signaling. Individual class I and class II proteins have different Shh concentration requirements for repression or activation.

(FIG. 8B) Cross-repressive interactions between class I and class II proteins that abut a common progenitor domain boundary refine and maintain progenitor domains.

(FIG. 8C) The profile of expression of class I and class II proteins within an individual progenitor domain controls neuronal fate.

Figure 9:
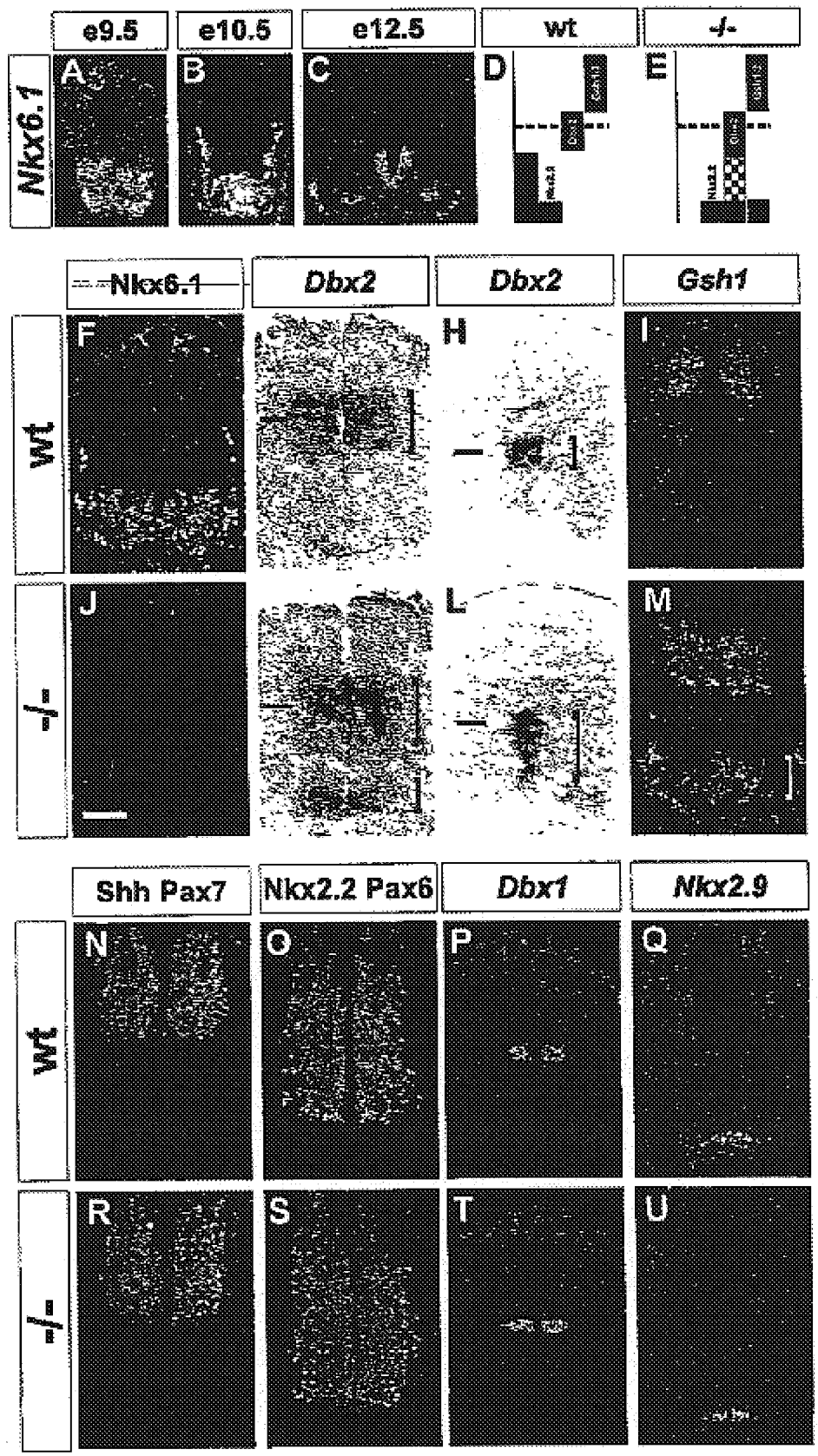

FIGS. 9A–9U Selective changes in homeobox gene expression in ventral progenitor cells in Nkx6.1 mutant embryos.

(FIGS. 9A–9C) Expression of Nkx6.1 in transverse sections of the ventral neural tube of mouse embryos. Expression of Nkx6.1 is prominent in ventral progenitor cells and persists in some post-mitotic motor neurons at both caudal hindbrain (FIG. 9B) and spinal cord (FIG. 9C) levels. (FIGS. 9D, and 9E) Summary diagrams showing domains of homeobox gene expression in wild type mouse embryos (FIG. 9D) and the change in pattern of expression of these genes in Nkx6.1 mutants (FIG. 9E), based on analyses at e10.0–e12.5. (FIGS. 9F–9I) Comparison of the domains of expression of Nkx6.1, Dbx2 and Gsh1 in the caudal neural tube of wild type e10.5 (FIGS. 9F, 9G, and 9I) and e12.5 (FIG. 9H) embryos. (FIG. 9J) Absence of Nkx6.1 protein expression in the ventral neural tube of an e10.5 Nkx6.1 mutant embryo. (FIGS. 9K–9M) Change in pattern of expression of Dbx2 and Gsh1 at e10.5 (FIGS. 9K and 9M) and of Dbx2 at e12.5 (9L) in the ventral neural tube of Nkx6.1 mutant embryos. (FIGS. 9N–9Q) Patterns of expression of Sonic hedgehog (Shh) (FIG. 9N), Pax7 (FIG. 9N), Nkx2.2 (FIG. 9O), Pax6 (FIG. 9P), Dbx1 (FIG. 9P) and Nkx2.9 (FIG. 9Q) in e10.5 wild type mouse embryos at spinal (FIGS. 9N–9P) and caudal hindbrain (FIG. 9Q) levels. Horizontal line in FIGS. 9G, 9H, 9K, and 9L indicates approximate position of the dorsoventral boundary of the neural tube, defined by Pax7 expression. Domains of high level Dbx2 and Gsh1 expression are shown by vertical lines in FIGS. 9G, 9H, 9K, 9L and 9M. (FIGS. 9R–9U). The patterns of Shh (FIG. 9R), Pax7 (FIG. 9R), Nkx2.2 (FIG. 9S), Pax6 (FIG. 9S), Dbx1 (FIG. 9T) and Nkx2.9 (FIG. 9U) expression are unchanged in e10.5 Nkx6.1 mutant embryos. Although the ventral limit of Pax6 expression is not changed in Nkx6.1 mutant embryos, the level of Pax6 expression by the most ventral progenitor cells is increased (FIG. 9S). Scale bar shown in J=100 μm (FIGS. 9A–9C); 50 μm (FIGS. 9F–9M); 60 μm (FIGS. 9N–9U).

Figure 10:
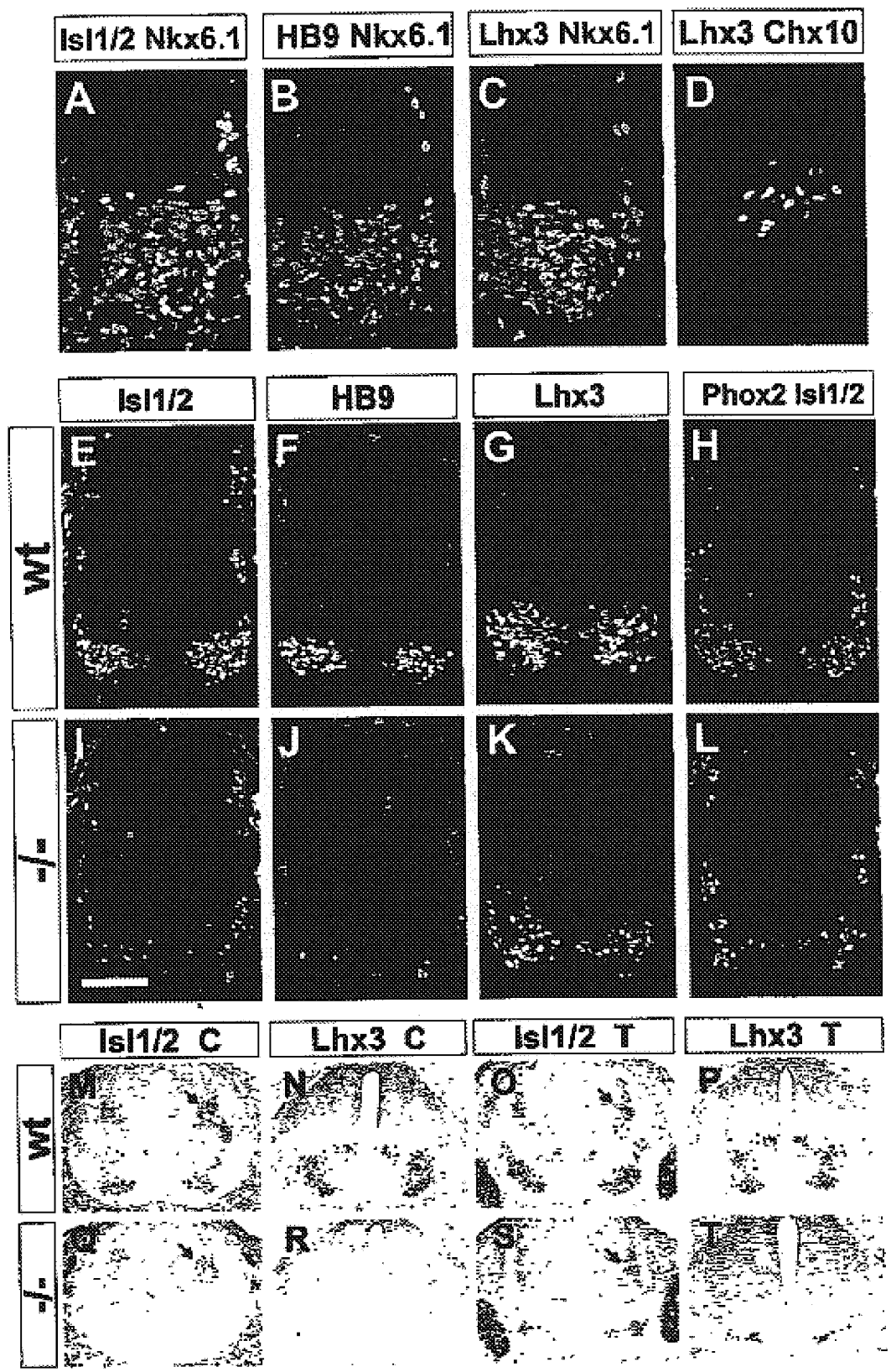

FIG. 10. Disruption of motor neuron differentiation in Nkx6.1 mutant embryos.

(FIG. 10A–10D) The relationship between the domain of Nkx6.1 expression by ventral progenitors and the position of generation of motor neurons and V2 interneurons in the ventral spinal cord of e10.5 wild type embryos. (FIG. 10A) Isl1/2 motor neurons (red) are generated within the Nkx6.1 (green) progenitor domain. (FIG. 10B) HB9 motor neurons (red) are generated from the Nkx6.1 (green) progenitor domain. (FIG. 10 C) Lhx3 (Lim3) expression (red) by motor neurons, V2 interneurons and their progenitors is confined to the Nkx6.1 progenitor domain. (FIG. 10D) Chx10 (green) V2 interneurons coexpress Lhx3 (red). (FIGS. 10E–10H) Expression of Isl1/2 (FIG. 10E), HB9 (FIG. 10F), Lhx3 (FIG. 10G) and Phox2a/b (FIG. 10H) in the ventral spinal cord (FIGS. 10E, 10F, 10G) and caudal hindbrain (FIG. 10H) of e10.5 wild type embryos. At cranial levels, Phox2a/b expression is restricted to visceral motor neurons (FIG. 10H). (FIGS. 10I–10L) A perturbation in the differentiation of motor neurons in e10.5 Nkx6.1 mutant embryos. (FIG. 10I) Few Isl1/2 motor neurons are detected at cervical spinal levels. (FIG. 10J) Few HB9 motor neurons are detected at cervical spinal levels. (FIG. 10K) A marked reduction in Lhx3 expression is detected at upper thoracic levels. (FIG. 10L) There is a marked reduction in the total number of Isl1/2 motor neurons at upper cervical/caudal hindbrain levels, but the number of Phox2a/b visceral motor neurons is not decreased. (FIGS. 10M–10P) Pattern of expression of Isl1/2 and Lhx3 at cervical (FIGS. 10M and 10N) and thoracic (FIGS. 10O and 10P) levels of e12.5 wild type embryos. Arrows in FIG. 10M and FIG. 10O indicate the position of Isl1 dorsal D2 interneurons. (FIGS. 10Q–10T) Absence of Isl1/2 and Lhx3 expression at cervical levels (FIGS. 10Q and 10R) and reduction in Isl1/2 and Lhx3 expression at thoracic levels (FIGS. 10S and 10T) in e12.5 Nkx6.1 mutant embryos. Scale bar shown in I=60 μm (FIGS. 10A–10D); 80 μm (FIGS. 10E–10L); 120 μm (FIGS. 10M–10T).

FIGS. 11A–11J Motor neuron subtype differentiation in Nkx6.1 mutant mice.

Figure 1:
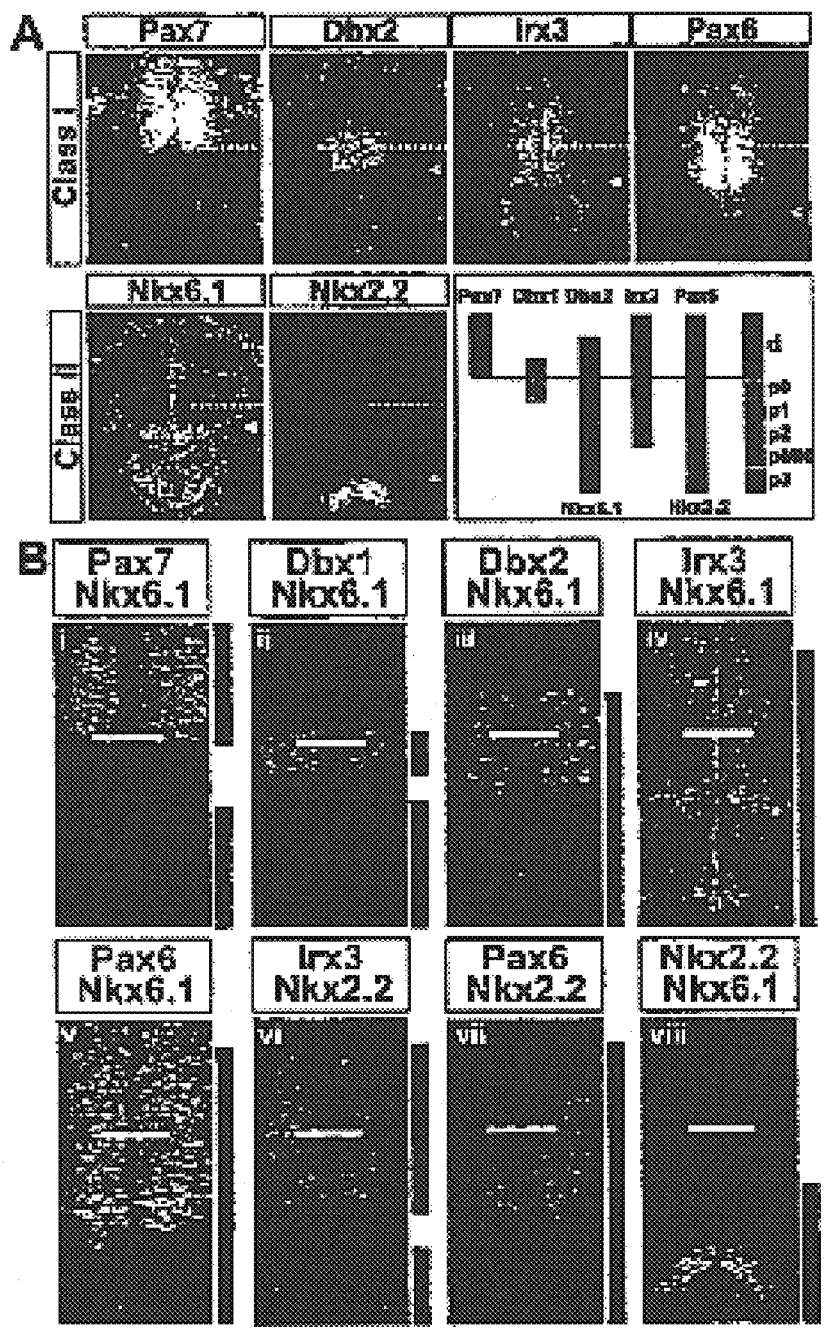
FIGS. 1A–1B Homedomain Proteins Define Five Ventral Progenitor Domains (FIG. 1A) Localization of homeo-domain proteins in the neural tube of HH stage 20 chick embryos. Class I proteins (Pax7, Dbx2, Irx3, Pax6) have different ventral boundaries (arrowheads). Class II proteins (Nkx6.1 and Nkx2.2) have different dorsal boundaries (arrowheads). The dorsoventral (DV) boundaries of the neural tube are indicated by dotted lines. Composite of expression domains shown in B. p=progenitor domain.
Figure 11:
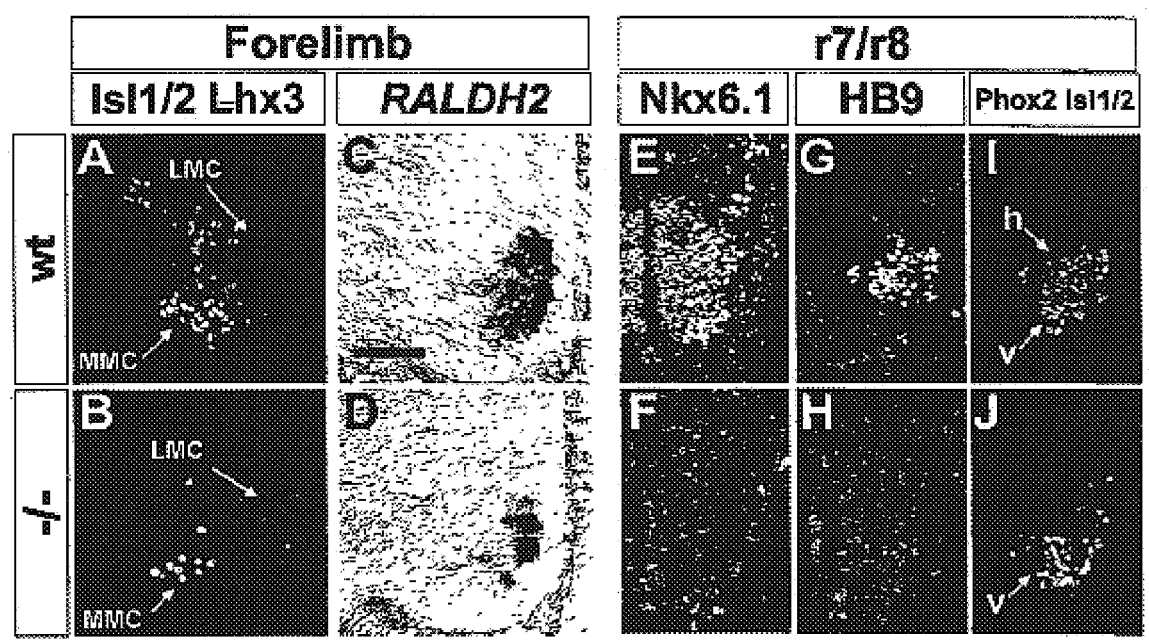

(FIGS. 11A and 11B) Depletion of both median motor column (MMC) and lateral motor column (LMC) neurons in Nkx6.1 mutant mice. Sections of e12.5 wild type (FIG. 11A) and Nkx6.1 mutant (FIG. 11B) mice spinal cord at forelimb levels show coexpression of Lhx3 (green) and Isl1/2 (red) in MMC (yellow) neurons and expression of Isl1/2 alone in LMC neurons. Both columnar subclasses of motor neurons are depleted in Nkx6.1 mutant mice. (FIGS. 11C and 11D) RALDH2 expression by LMC neurons in e12.5 forelimb level spinal cord of wild type (FIG. 1C) and Nkx6.1 mutant (FIG. 11D) mice. (FIGS. 11E–11J) Motor neuron generation at caudal hindbrain (rhombomere [r] 7/8) level. (FIGS. 11E and 11F) Pattern of Nkx6.1 expression in progenitor cells and visceral motor neurons in the caudal hindbrain of e10.5-e11 wild type mice (FIG. 11E) and absence of protein expression in Nkx6.1 mutant mice (FIG. 11F). (FIGS. 11G and 11H) HB9 expression in hypoglossal motor neurons in e10.5-e11 wild type mice (FIG. 11G) is lacking in Nkx6.1 mutant mice (FIG. 11H). (FIGS. 11I and 11J) In e10.5-e11 wild type mice (FIG. 11I) visceral vagal motor neurons (v) coexpress Isl1 (green) and Phox2a/b (red) whereas hypoglossal motor neurons (h) lack Phox2a/b expression. In e11 Nkx6.1 mutant mice (FIG. 11J) visceral vagal motor neurons (v) persist in normal numbers but hypoglossal motor neuronal are absent. Scale bar shown in C=50 μm (FIGS. 11A–11D); 70 μm (FIGS. 11E–11J).

FIGS. 12A–12L A switch in ventral interneuron fates in Nkx6.1 mutant mice.

Figure 12:
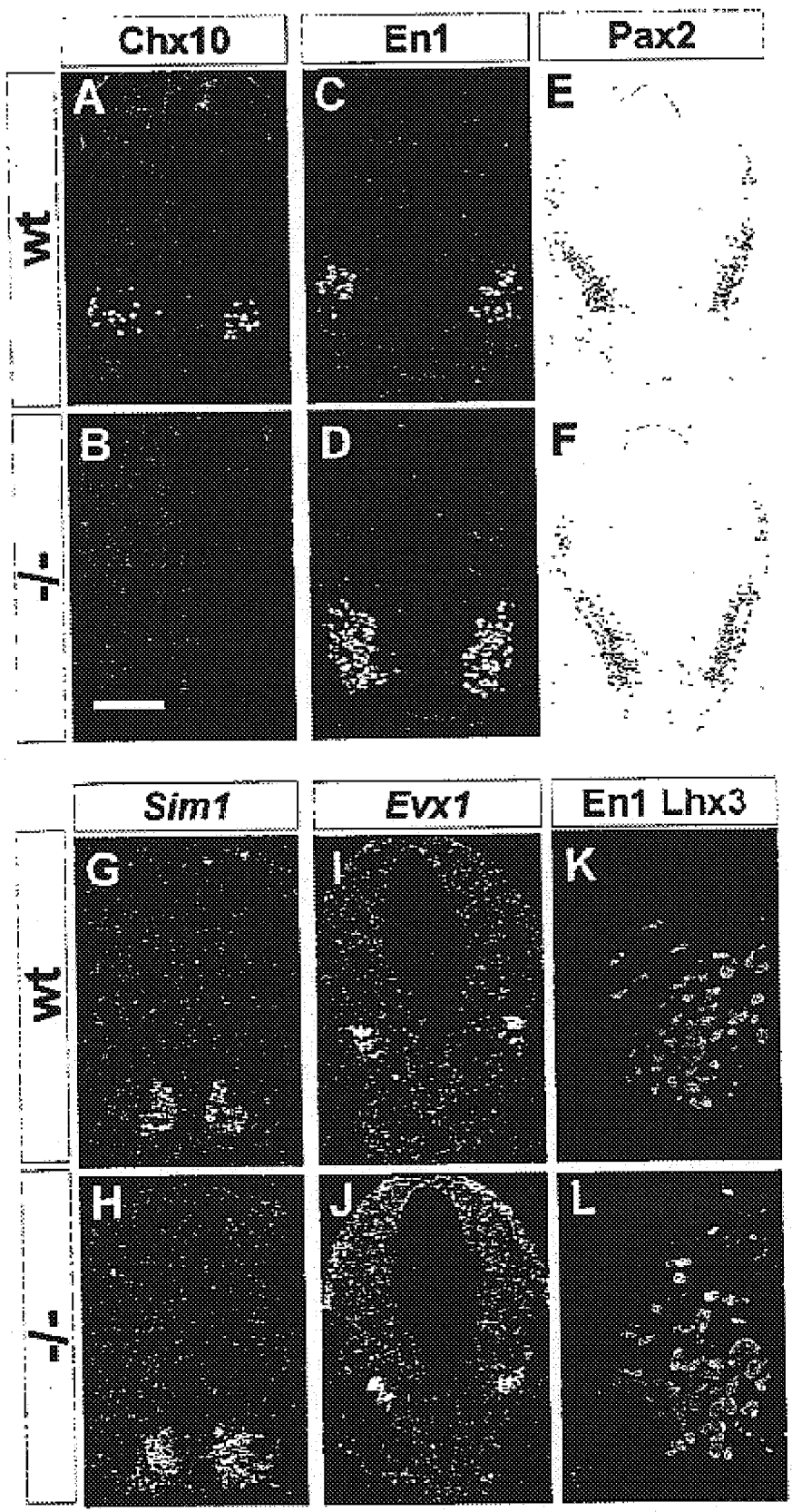

(FIGS. 12A and 12B) Chx10 expression in V2 neurons at rostral cervical levels of an e10.5 wild type embryo (FIG. 12A) and the absence of expression of Chx10 in Nkx6.1 mutant embryos (FIG. B12). (FIGS. 12C and 12D) Expression of En1 by V1 neurons at rostral cervical levels of an e10.5 wild type embryo (FIG. 12C) and the ventral expansion of the domain of V1 neuron generation in Nkx6.1 mutant embryos (FIG. 12D). (FIGS. 12E and 12F) Pax2 expression in a set of interneurons that includes V1 neurons (21) at caudal hindbrain levels of an e10.5 wild type embryo (FIG. 12E) and the ventral expansion of the domain of Pax2 expression in Nkx6.1 mutant embryos (FIG. 12F). (FIGS. 12G and 12H) Expression of Sim1 by V3 neurons in the cervical spinal cord of an e10.5 wild type (FIG. 12G) and Nkx6.1 mutant (FIG. 12H) embryos.

(FIGS. 12I and 12J) Expression of Evx1 by V0 neurons at caudal hindbrain levels of e10.5 wild type (FIG. 12I) and Nkx6.1 mutant (FIG. 12J) embryos. (FIG. 12K and 12L) En1 (red) and Lhx3 (green) expression by separate cell populations in the ventral spinal cord of e11 wild type embryos (FIG. 12K). In Nkx6.1 mutant embryos (FIG. 12L) coexpression of En1 and Lhx3 is detected in many cells within the normal domain of V2 neuron generation. Scale bar shown in B=60 $\mu$m (FIGS. 12A–12D); 75 $\mu$m (FIGS. 12E, 12F); 70 $\mu$m (FIGS. 12G, 12J, 12H, 12J), 35 $\mu$m (FIGS. 12K and 12L).

Figure 13:
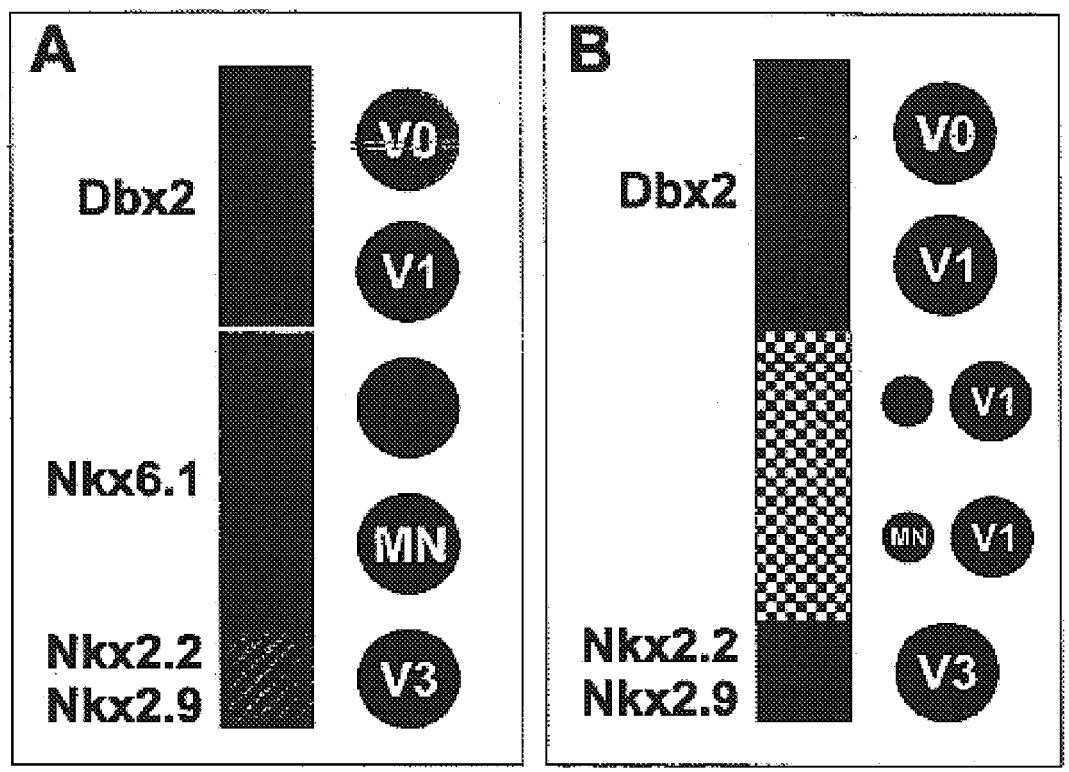

FIGS. 13A–13B Summary of changes in progenitor domain identity and neuronal fate in the spinal cord of Nkx6.1 mutant embryos.

(FIG. 13A). In wild type mouse embryos, cells in the Nkx6.1 progenitor domain give rise to three classes of ventral neurons: V2 neurons, motor neurons (MN) and V3 neurons. V3 neurons derive from cells in the ventral most region of Nkx6.1 expression that also express Nkx2.2 and Nkx2.9. V1 neurons derive from progenitor cells that express Dbx2 but not Nkx6.1. (FIG. 13B). In Nkx6.1 mutant embryos the domain of Dbx2 expression by progenitor cells expands ventrally, and by e12 occupies the entire dorsoventral extent of the ventral neural tube, excluding the floor plate. Checked area indicates the gradual onset of ventral Dbx2 expression. This ventral shift in Dbx2 expression is associated with a marked decrease in the generation of V2 neurons and motor neurons and a ventral expansion in the domain of generation of V1 neurons. The generation of V3 neurons (and cranial visceral motor neurons at hindbrain levels) is unaffected by the loss of Nkx6.1 or by the ectopic expression of Dbx2.

DETAILED DESCRIPTION OF THE INVENTION

This invention provides a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein. In an embodiment of the above-described genetically engineered stem cell, the neural stem cell is a mammalian neural stem cell. In a preferred embodiment, the mammalian stem cell is a human neural stem cell.

This invention provides a method of generating a genetically engineered motor neuron which is capable of expressing homeodomain transcription factor Nkx6.1 protein but does not express homeodomain transcription factor Irx3 protein or homeodomain transcription factor Nkx2.2 protein which comprises treating a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein under conditions such that the retroviral expression system expresses homeodomain transcription factor Nkx6.1 protein so as to thereby generate the genetically engineered motor neuron. In an embodiemnt of the above-described method of generating a genetically engineered motor neuron which is capable of expressing homeodomain transcription factor Nkx6.1 protein but does not express homeodomain transcription factor Irx3 protein or homeodomain transcription factor Nkx2.2 protein, the neural stem cell is a mammalian cell neural stem cell. In a preferred embodiment, the mammalian neural stem cell is a human neural stem cell.

This invention provides a genetically engineered cell comprising a neural stem cell and retroviral expression system in the neural stem cell, which is capable of expressing homeodomain transcription factor Nkx6.1 protein and homeodomain transcription factor Irx3 protein. In an embodiemnt of the above-described genetically engineered stem cell, the neural stem cell is a mammalian neural stem cell. In a preferred embodiment of the genetically engineered cell, wherein the mammalian neural stem cell is a human neural stem cell.

This invention provides a method of generating a genetically engineered V2 neuron which is capable of expressing homeodomain transcription factor Nkx6.1 protein and homeodomain transcription factor Irx3 protein which comprises treating a genetically engineered cell comprising a neural stem cell and retroviral expression system in the neural stem cell, which is capable of expressing homeodomain transcription factor Nkx6.1 protein and homeodomain transcription factor Irx3 protein, under conditions such that the retroviral expression system expresses homeodomain transcription factor Nkx6.1 protein and homeodomain transcription factor Irx3 protein so as to thereby generate the genetically engineered V2 neuron. In an embodiment of the above-described method of generating a genetically engineered V2 neuron which is capable of expressing homeodomain transcription factor Nkx6.1 protein and homeodomain transcription factor Irx3 protein, the neural stem cell is a mammalian neural stem cell. In a preferred embodiment, the mammalian neural stem cell is a human neural stem cell.

This invention provides a genetically engineered cell comprising a neural stem cell and retroviral expression system in the neural stem cell, which is capable of expressing homeodomain transcription factor Nkx2.2 protein or homeodomain transcription factor Nkx2.9 protein. In an embodiment of the above-described genetically engineered cell the neural stem cell is a mammalian neural stem cell. In a preferred embodiment, the mammalian neural stem cell is a human neural stem cell.

This invention provides a method of generating a genetically engineered V3 neuron which is capable of expressing homeodomain transcription factor Nkx2.2 protein or homeodomain transcription factor Nkx2.9 protein which comprises treating a genetically engineered cell comprising a neural stem cell and retroviral expression system in the neural stem cell, which is capable of expressing homeodomain transcription factor Nkx2.2 protein or homeodomain transcription factor Nkx2.9 protein, under conditions such that the retroviral expression system expresses homeodomain transcription factor Nkx2.2 protein or homeodomain transcription factor Nkx2.9 protein so as to thereby generate the genetically engineered V3 neuron. In an embodiment of the above-described method of generating a genetically engineered V3 neuron which is capable of expressing homeodomain transcription factor Nkx2.2 protein or homeodomain transcription factor Nkx2.9 protein, the neural stem cell is a mammalian neural stem cell. In a preferred embodiment, the mammalian neural stem cell is a human neural stem cell.

In the practice of the methods described herein one of skill may use any suitable retroviral vector t express the desired protein(s).

This invention provides a method of treating a subject having a motor neuron injury or a motor neuron disease comprising: implanting in injured or diseased neural tissue of the subject a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein. In an embodiment of the above-described method of treating subject having a motor neuron injury or a motor neuron disease the neural stem cells are transfected with the retroviral expression system ex vivo and implanted into the subject. In another embodiment of the above-described method the neural stem cells are transfected with the retroviral expression system in vitro and implanted into the subject. In a further embodiment of the above-described method the motor neuron disease is amyotrophic lateral sclerosis (AML), spinal muscular atrophy (SMA) or any motor neuron degenerative disease. In a preferred embodiment of the above-described method the neural stem cells are from the developing mammalian nervous system. In another preferred embodiment of the above-described method the neural stem cells are from the adult mammalian nervous system. The nervous system may be from any mammal including human. The genetically engineered implanted cells will express homeodomain transcription factor Nkx6.1 protein and thereby generate motor neurons. The genetically engineered implanted cells may also affect endogenous neural stem cells into generating motor neurons.

This invention provides a method of treating a subject having a motor neuron injury or a motor neuron disease comprising: administering to injured or diseased neural tissue of adult spinal cord a retroviral expression system, which is capable of expressing homeodomain transcription factor Nkx6.1 protein but does not express homeodomain transcription factor Irx3 protein or homeodomain transcription factor Nkx2.2 protein. In an embodiment of the above-described method of treating subject having a motor neuron injury or a motor neuron disease the motor neuron injury may be a spinal cord injury. In another embodiment of the above-described method the motor neuron disease is amyotrophic lateral sclerosis, spinal muscular atrophy (SMA) or any other motor neuron degenerative disease. The retroviral expression system will express homeodomain transcription factor Nkx6.1 protein and thereby generate motor neurons in endogenous neural stem cells of the adult spinal cord or in the injured or diseased neural tissue of adult spinal cord.

This invention provides-a method of treating a subject having a motor neuron injury or a motor neuron disease comprising: a) transfecting neural stem cells with a retroviral vector, which is capable of expressing homeodomain transcription factor Nkx6.1 protein but does not express homeodomain transcription factor Irx3 protein or homeodomain transcription factor Nkx2.2 protein; and b) injecting the transfected neural stem cells of step (a) into the central canal of the spinal cord under conditions which allow the injected transfected neural stem cells to be incorporated into the ependimal layer of the spinal cord. In an embodiment of the above-described method the neural stem cells are from the developing mammalian nervous system. In a preferred embodiment, the neural stem cells are from the adult mammalian nervous system. The subject may be any mammal including a human. In the above-described method the transfected neural stem cells will generate motor neurons in the ependimal layer of the spinal cord which are in/near the central canal.

Since neural stem cells exist not only in the developing mammalian nervous system but also in the adult nervous system of all mammalian organisms, including humans (see Gage, F. H., Science 287:1433— (2000)), the above-described method is useful in any stem cell based therapy to control the neural cell types that generated by a stem cell to ensure replacement of the appropriate cells or repair of injured cells. For example, any of the above-described genetically engineered cells may be transplanted into a human suffering from a neurodegenerative disease (including but not limited to ALS or SMA) or injuries in the nervous system, e.g. spinal cord, to replace missing or injured cells in the subject or to repair endogenous stem cells in the subject, e.g. neural stem cells genetically engineered to produce motor neurons by expression of the appropriate homeodomain protein code in vivo or ex vivo. (see also Doetsch, F. et al. (1999) Cell 97(6):703–716 and Johansson C. B. et al. (1999) Cell 96(1):25–34) Any of the above-described genetically engineered cell lines, especially motor neurons, are also useful for in vivo or in vitro studies in pharmaceutical assays to determine which compounds which induce, increase, decrease, or inhibit generation of a motor neuron from a neural stem cell.

One of skill is familiar with techniques which introduce stem cells into the spinal cord, as well as conditions under which the introduced stem cells will performed the desired protein expression, such as those used in treatment of Parkinson's disease. Techniques and conditions such as these may be implemented in the practice of the methods described herein.

The genes studied herein, including Nkx6.1 which encodes homeodomain transcription factor Nkx6.1 protein, are highly conserved in mammalian cells. Therefore, the experiments set forth herein are the basis of genetic engineering of human neural stem cells (progenitor cells) to enable generation of motor neurons, or V2 and V3 neurons, which are used in motor control, in the treatment of motor neuron degenerative diseases or neural disease in which the genes encoding the proteins required for their generation are either missing or mutated.

This invention provides a method of determining whether a chemical compound affects the generation of a motor neuron from a neural stem cell which comprises: a) contacting a genetically engineered cell comprising a neural stem cell and retroviral expression system in the neural stem cell, which is capable of expressing homeodomain transcription factor Nkx6.1 protein but does not express homeodomain transcription factor Irx3 protein or homeodomain transcription factor Nkx2.2 protein with the chemical compound under conditions such that in the absence of the compound the neural stem cell expresses homeodomain transcription factor Nkx6.1 protein and generates a motor neuron; and b) determining what effect, if any, the compound has on generation of the motor neuron. In an embodiment of the above-described method of determining a chemical compound affects the generation of a motor neuron from a neural stem cell the chemical compound promotes generation of the motor neuron. In another embodiment of the above-described method of determining whether a chemical compound affects the generation of a motor neuron from a neural stem cell the chemical compound inhibits generation of the motor neuron.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

Experimental Procedures

Retroviral Transduction and In Ovo Electroporation

Mouse Nkx2.2, Nkx2.9, Nkx6.1, chick Dbx2 and GFP cDNAs were cloned into RCASBP(A) and (B) vectors (Hughes et al., 1987; Morgan and Fekete, 1996). Viral supernatants (Morgan and Fekete, 1996) were applied to Hamburger-Hamilton (1951) (HH) stage 5–6 chick embryos in ovo. Retroviral transduction resulted in expression of the target protein 12–14 h post-infection (data not shown). For electroporation cDNAs were cloned into RCASBP or pNES (gift of U. Lendhal) vectors. HH stage 10–12 chick embryos were electroporated unilaterally with cDNAs for mouse Irx3, Pax6, RCASBP(Dbx2) and RCASBP(GFP) using a T820 electro-squareporator (BTX Inc) and ectopic protein expression was detected after 2–4 h. Embryos were analyzed at HH stages 20–24.

Immunocytochemistry and In Situ Hybridization Histochemistry

Guinea-pig antisera were generated against peptides encoding the N-terminal 14 residues of mouse Irx3 and the N-terminal 12 residues of mouse Nkx2.9. Other antibody reagents and protocols have been described (Yamada et al., 1993; Ericson et al, 1997a; Tanabe et al., 1998; Pierani et al., 1999; Briscoe et al., 1999). In situ hybridization was performed as described (Schaeren-Wiemers and Gerfin-Moser, 1993), using probes for Irx3, Nkx2.2, Sim1, Nkx6.1 and Nkx2.9 (Briscoe et al., 1999).

BrdU Incorporation

To define mitotic cells, 100 $\mu$M BrdU was applied to HH stage 22 embryos, followed by incubation at 37° C. for 30 min, at which time embryos were fixed and analyzed.

Neural Explant Culture

Neural explants were isolated from intermediate [i] regions of stage 10 chick neural plate or ventral+floor plate [vf] regions from stage 10 or stage 15 embryos, as described (Yamada et al., 1993; Ericson et al., 1996). Explants were cultured for 24 h with or without Shh-N (Ericson et al., 1996), or in the presence of anti-Shh IgG (20 $\mu$g/ml; Ericson et al., 1996). Explants were processed as described (Ericson et al., 1997a).

Results

A Homeodomain Protein Code for Ventral Progenitor Cells Shh signaling controls the generation of five distinct classes of neurons, each at a different dorsoventral position in the ventral neural tube (Briscoe et al., 1999; Ericson et al., 1997a; Pierani et al., 1999). The spatial information provided by the five homeodomain proteins examined previously—Pax7, Dbx1, Dbx2, Pax6 and Nkx2.2—is not sufficient to establish distinct progenitor domains for each post-mitotic neuronal subtype (Ericson et al., 1996; Ericson et al., 1997a; Briscoe et al., 1999; Pierani et al., 1999), prompting a search for other relevant homeodomain proteins. It was found that two additional proteins, Nkx6.1 (Qiu et al., 1998) and Irx3 (Funayama et al., 1999), are expressed by distinct sets of ventral progenitor cells.

Compared were the patterns of expression of Nkx6.1 and Irx3 with the homeodomain proteins characterized previously. The combinatorial expression of this set of seven homeodomain proteins is sufficient to define five ventral progenitor cell (p) domains, which are termed the p0, p1, p2, pMN and p3 domains, in dorsal-to-ventral progression (FIG. 1A). The ventral limit of Pax7 expression defines the dorsal/p0 boundary (FIG. 1Bi; Ericson et al., 1996); the ventral limit of Dbx1 expression defines the p0/p1 boundary (FIG. 1Bii; Pierani et al., 1999); the ventral limit of Dbx2 expression defines the p1/p2 boundary (FIG. 1Biii; Pierani et al., 1999); the ventral limit of Irx3 expression defines the p2/pMN boundary (FIG. 1Biv, vi); and the ventral limit of Pax6 expression defines the pMN/p3 boundary (FIG. 1Bv, vii; Ericson et al., 1997a). The dorsal limit of Nkx6.1 expression complements the ventral limit of Dbx2 expression at the p1/p2 boundary (FIG. 1Biii); and the dorsal limit of Nkx2.2 expression complements the ventral limit of Pax6 expression at the pMN/p3 boundary (FIG. 1bvii; Ericson et al., 1997a).

These seven homeodomain proteins can therefore be divided into two major subclasses. Five proteins—Pax7, Dbx1, Dbx2, Irx3 and Pax6—exhibit ventral limits of expression that delineate progenitor domain boundaries, and these are termed class I proteins (FIG. 1A). Two proteins—Nkx6.1 and Nkx2.2—exhibit dorsal limits of expression that define progenitor domain boundaries, and these are termed class II proteins (FIG. 1A).

Progenitor Homeodomain Protein Expression is Initiated by an Early Period of Graded Sonic Hedgehog Signaling The expression of certain class I (Pax7, Dbx1, Dbx2, Pax6) and class II (Nkx2.2) proteins is controlled by Shh signaling in vitro (Ericson et al., 1996; Ericson et al., 1997a; Briscoe et al., 1999; Pierani et al., 1999). The expression of class I proteins is repressed by Shh signaling, and the more ventral the boundary of class I protein expression in vivo, the higher is the concentration of Shh required for repression of protein expression in vitro (Ericson et al., 1997a). Conversely, Shh signaling is required to induce expression of the class II protein Nkx2.2 in vitro (Briscoe et al., 1999; Ericson et al., 1997a).

Figure 2:
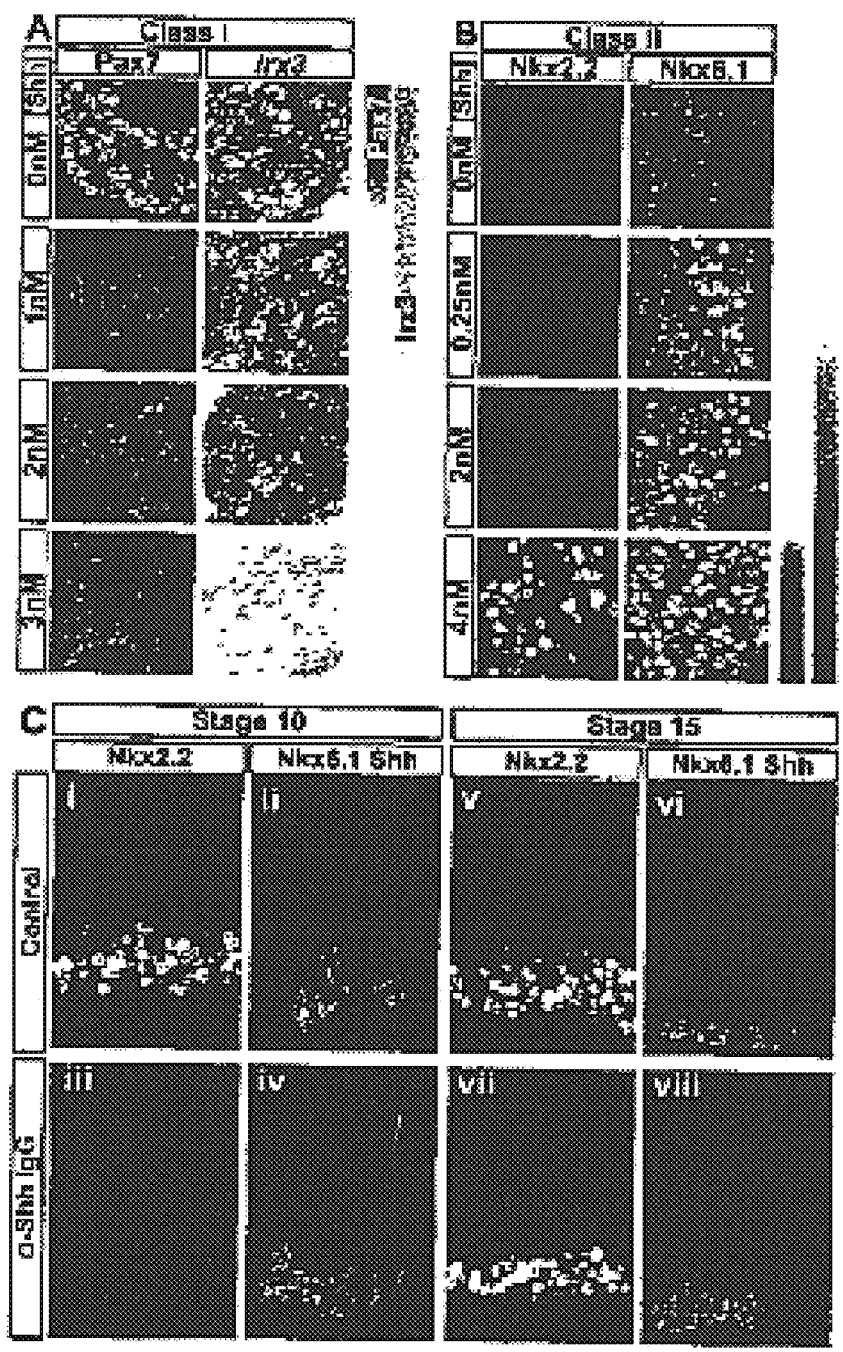
FIGS. 2A–2C Shh Signaling is Required to Establish but not to Maintain the Expression of Progenitor Homeodomain Proteins.

Examined was whether this relationship extends to Irx3 and Nkx6.1 by assaying the expression of these two proteins in intermediate neural plate [i] explants exposed to different Shh-N concentrations. Repression of Irx3 required ~3 nM Shh-N (FIG. 2A), a concentration greater than that required for repression of Pax7, Dbx1 and Dbx2 expression (FIG. 2A; Ericson et al., 1996; Pierani et al., 1999), but less than that required for complete repression of Pax6 (Ericson et al., 1997a). Conversely, induction of Nkx6.1 required ~0.25 nM Shh-N; a concentration lower than that required for induction of Nkx2.2 (3–4 nM; Ericson et al., 1997a; FIG. 2B). Thus, the link between the domains of expression of class I and class II proteins in vivo and the Shh concentration that regulates their expression in vitro extends to Irx3 and Nkx6.1 (FIG. 2A, B). These findings support the idea that the differential patterns of expression of all class I and class II proteins depend initially on graded Shh signaling.

Next asked was whether Shh signaling is required continuously to maintain the early pattern of progenitor homeodomain protein expression. To address this examined was whether the expression of class II proteins, once initiated, can be maintained under conditions in which ongoing Shh signaling is eliminated. Explants of ventral neural tube, including the floor plate, ([vf] explants) were isolated from stage 10 or stage 15 embryos and grown in vitro, alone or in the presence of a function blocking anti-Shh antibody (Ericson et al., 1996). Both stage 10 and stage 15 [vf] explants grown alone generated a narrow domain of Nkx2.2$^+$ cells and a broad domain of Nkx6.1$^+$ cells (FIGS. 2Ci, ii, v, vi). Addition of anti-Shh IgG to stage 10 [vf] explants blocked the expression of both Nkx2.2 and Nkx6.1 in neural progenitors (FIGS. 2Ciii, iv). In contrast in stage 15 [vf] explants, the domains of Nkx2.2 and Nkx6.1 expression persisted in the presence of anti-Shh IgG (FIGS. 2Cvii, viii). These results provide evidence that the pattern of class II protein expression becomes independent of Shh signaling over a period of ~12–15 h, between stages 10 and 15.

Cross-Repressive Interactions Between Class I and Class II Proteins Refine Progenitor Domain Boundaries The boundaries of progenitor domains are sharply delineated in vivo (FIG. 1), raising questions about the steps that operate downstream of Shh signaling to establish the non-graded domains of expression of class I and class II proteins. Examined was whether the domain of expression of class I proteins might be constrained by the action of the class II protein that abuts the same domain boundary, and vice versa. To test this, individual homeodomain proteins in the chick neural tube were misexpressed in mosaic fashion, and the resulting pattern of class I and class II protein expression was assayed. Ectopic protein expression was achieved using either retroviral transduction or electroporation.

Interactions at the p3/pMN Boundary

First analyzed was the interaction between the class I protein Pax6 and the class II protein Nkx2.2—proteins that exhibit complementary domains of expression at the pMN/p3 boundary. To assess the influence of Pax6 on Nkx2.2, Pax6 was misexpressed ventral to its normal limit and the resulting pattern of expression of Nkx2.2 was examined (FIGS. 3A–C). After electroporation of Pax6, small clusters of ectopic Pax6 cells were detected within the p3 domain (FIGS. 3A, 3B). These cells lacked Nkx2.2 expression (FIGS. 3A, 3B), whereas expression of Nkx2.2 was maintained by neighboring p3 domain cells that lacked ectopic Pax6 expression (FIGS. 3A, 3B), arguing for a cell-autonomous action of Pax6. The expression of other class I and class II proteins was not affected by the deregulated expression of Pax6 (data not shown). Thus, Pax6 acts selectively to repress Nkx2.2 expression in p3 domain cells. These results complement studies showing a requirement for Pax6 activity in defining the dorsal limit of the p3 domain in vivo (Ericson et al., 1997a).

To examine whether Nkx2.2 normally limits the ventral boundary of Pax6 expression, Nkx2.2 was misexpressed in regions dorsal to the p3 domain. The vast majority (>95%) of progenitor cells that ectopically expressed Nkx2.2 lacked Pax6 expression (FIG. 3D). Since these experiments used a replication competent retroviral expression system, the coexpression of both homeodomain proteins in a small minority of cells is likely to reflect the secondary infection of cells at later stages, with the consequence that Nkx2.2 may be expressed for too brief a period to repress Pax6 completely. Neighboring cells that lacked ectopic Nkx2.2 retained Pax6 expression (FIG. 3D), indicating a cell-autonomous action of Nkx2.2. The expression of Nkx6.1 and Pax7 was unaffected by the ectopic expression of Nkx2.2 (FIGS. 3E, 3F). Thus, the repressive action of Nkx2.2 on Pax6 expression is selective and cell-autonomous. These results provide evidence for mutually repressive interactions between Pax6 and Nkx2.2 at the pMN/p3 boundary.

Nkx2.9, a gene closely related to Nkx2.2 (Pabst et al., 1998), is expressed in a pattern that overlaps transiently with Nkx2.2 in the p3 domain (Briscoe et al., 1999). To test whether these two genes have similar activities, Nkx2.9 was expressed ectopically and the pattern of Pax6 expression was examined. Most (>95%) cells that expressed Nkx2.9 ectopically lacked Pax6 expression (FIG. 3G). Moreover, the repression of Pax6 occurred in the absence of Nkx2.2 induction (FIG. 3H), showing that Nkx2.9 acts independently of Nkx2.2. Thus, Nkx2.2 and Nkx2.9 have similar abilities to repress Pax6 expression and are likely to act in parallel in defining the ventral boundary of the pMN domain in vivo (Briscoe et al., 1999).

Interactions at the p1/p2 Boundary

Next examined was whether cross-regulatory interactions occur between the class I protein Dbx2 and the class II protein Nkx6.1—proteins with complementary domains of expression at the p1/p2 boundary. First Dbx2 was misexpressed in regions ventral to the p1 domain and the pattern of homeodomain protein expression was monitored. Most (>95%) ventral cells that ectopically expressed Dbx2 lacked expression of Nkx6.1 (FIG. 3J), whereas neighboring cells that lacked Dbx2 maintained Nkx6.1 expression (FIG. 3J). Misexpression of Dbx2 did not alter the expression of Pax6 or Pax7 (FIGS. 3K, 3L). Thus, the repressive action of Dbx2 is selective and cell-autonomous. Also examined was the consequences of misexpression of Nkx6.1 on the expression of Dbx2. Most (>95%) progenitor cells that ectopically expressed Nkx6.1 lacked Dbx2 expression (FIG. 3M), whereas neighboring cells that lacked ectopic Nkx6.1 maintained Dbx2 expression (FIG. 3M). Ectopic expression of Nkx6.1 did not repress Pax6 or Pax7 (FIGS. 3N, 3O). Thus, Nkx6.1 acts selectively and in a cell-autonomous manner to repress Dbx2 expression.

These results reveal that the two pairs of class I and class II proteins that share a common progenitor domain boundary exhibit mutual repressive interactions. Such interactions are likely to contribute to the establishment and sharp delineation of progenitor domain boundaries evident in vivo.

The Relationship Between Progenitor Domain and Neuronal Fate

Next examined was the relationship between the five progenitor domains defined by class I and class II protein expression and the pattern of neurogenesis in the ventral neural tube. It was found previously that Evx1/2$^+$ V0 neurons derive from cells within the p0 domain (see Pierani et al., 1999; Ericson et al., 1997a), that En1$^+$ V1 neurons derive from cells within the p1 domain (Ericson et al., 1997a; Pierani et al., 1999) (FIGS. 4D and 4E) and that Sim1$^+$ V3 neurons derive from cells within the p3 domain (Briscoe et al., 1999). It is shown here that Chx10$^+$ V2 neurons derive exclusively from cells within the p2 domain (FIGS. 4B and 4C) (Ericson et al., 1997a) and that HB9$^+$ motor neurons (MNs) derive only from cells within the pMN domain (FIGS. 4A and 4E) (Tanabe et al., 1998). Thus, a precise register exists throughout the neural tube between the dorsoventral extent of individual ventral progenitor domains and the position at which specific neuronal subtypes are generated.

Progenitor cells express a separate set of homeodomain proteins at late stages in the pathway of ventral neurogenesis. The final division of V2 neuron and MN progenitors is accompanied by the onset of expression of Lim3 (Ericson et al., 1997a; Sharma et al., 1998; Tanabe et al., 1998). Late stage MN progenitors express MNR2 (Tanabe et al., 1998). Lim3 and MNR2 appear to function respectively as determinants of V2 neuron and MN identity (Sharma et al., 1998; Tanabe et al., 1998). Therefore, examined was whether the expression of Lim3 and MNR2 also conforms to the domains defined by class I and class II protein expression. Lim3 expression was excluded from the p0 and p1 domains but was detected within both the p2 and pMN domains (FIGS. 4F and 4G and data not shown), whereas MNR2 expression was confined to the pMN domain (FIGS. 4H–4J). Thus, the expression of these two ventral neuronal subtype determinants also respects progenitor domain subdivisions defined by class I and class II protein expression. The concordance in expression of progenitor homeodomain proteins, late stage progenitor determinants and neuronal fate supports the idea that the subdivision of the neural epithelium into five progenitor domains is a fundamental step in the allocation of cell fate in the ventral neural tube.

Nkx6.1 Activity Directs Motor Neuron and V2 Neuron Generation

If the combinatorial expression of class I and class II proteins within progenitor cells directs the fate of ventral neurons, then changing the expression profile of these proteins would be expected to alter patterns of neurogenesis. The analysis of this issue was focused on the three ventral-most progenitor domains, from which V2 neurons, MNs and V3 neurons are generated (FIG. 4K). The combinatorial expression of Nkx6.1, Irx3 and Nkx2.2 distinguishes these three domains of neurogenesis (FIG. 4L), and poses three questions about their role in the assignment of neuronal subtype identity. First, is whether the expression of Nkx6.1 in the absence of expression of Irx3 or Nkx2.2/Nkx2.9 sufficient to result in the generation of MNs. Second, is whether the coincidence in expression of Nkx6.1 and Irx3 result in the generation of V2 neurons, at the expense of MNs. Third, is whether the expression of Nkx2.2/Nkx2.9 and Nkx6.1 result in the generation of V3 neurons rather than MNs.

To test whether Nkx6.1 activity is able to generate MNs, a way of misexpressing Nkx6.1 in neural progenitor cells in the absence of high level Irx3 expression was searched. All progenitor cells dorsal to the p2/pMN boundary express Irx3 (data not shown). The onset of Irx3 expression occurs only after neural tube closure, later than that of Nkx6.1 and is excluded from the ventral-most region of the neural tube (Supplemental FIG. S1; available at http://www.cell.com/cgi/content/full/101/4/■■■/DC1)). It was reasoned therefore that misexpression of Nkx6.1 by dorsal neural cells, prior to the onset of Irx3 expression, might establish an initial homeodomain protein code (Nkx6.1$^-$, Irx3$^-$) that mimics that found normally in the pMN domain, and thus lead to ectopic MN generation.

Two approaches were taken to achieve early ectopic expression of Nkx6.1. First, Nkx6.1 was misexpressed in stage 5–6 embryos by retroviral transduction (FIG. S1A). With this method the onset of ectopic protein expression occurs about 12–16 h later, at approximately stages 12–14 (FIG. S1B). At this stage, only at the most caudal levels of infected embryos was ectopic neural expression of Nkx6.1 detected before the onset of expression of Irx3 (FIG. S1C). At more rostral levels, the onset of ectopic protein expression occurs at a stage when neural cells already express Irx3 (FIG. S1D). Nkx6.1 was also misexpressed by electroporation in stage 10 embryos (FIG. S1E). In this case, expression of transgenes was detected within ~2–4 h (FIG. S1F; Muramatsu et al., 1997). Under these conditions, Nkx6.1 was expressed ectopically prior to the onset of Irx3 expression over a broader rostrocaudal region of the neural tube (FIGS. S1F–S1H). Based on these observations, embryos that had been retrovirally infected or electroporated in ovo with Nkx6.1 constructs were permitted to develop until stages 22–24, and the resulting pattern of neurogenesis was examined.

First examined were levels of the neural tube where ectopic dorsal neural expression of Nkx6.1 occurred prior to that of endogenous Irx3. At these levels, the MN subtype determinants MNR2 and Lim3 were detected in ectopic dorsal positions, in both progenitor cells and post-mitotic neurons (FIGS. 5A ix and 5Ax and data not shown). In addition, ectopic dorsal expression of the post-mitotic MN markers Isl1, Isl2 and HB9 was detected (FIGS. 5Axi–5Axiii and data not shown). The ectopic expression of Isl1, Isl2 and HB9 was, however, limited to post-mitotic MNs located in the lateral margin of the neural tube (FIGS. 5Axi–5Axiii). This finding is consistent with previous studies documenting that MNR2 can induce these MN markers only after cells have acquired post-mitotic status (Tanabe et al., 1998). Strikingly, the expression of MN markers was detected both dorsal to the p2 domain boundary in the ventral neural tube, and throughout the dorsal extent of the neural tube (FIG. 5A and data not shown). Under these conditions, additional ectopic Chx10$^+$ V2 neurons were occasionally detected within the p0 and p1 domains, but were not detected in the dorsal spinal cord (FIG. 5A xiv and see below). These results show that misexpression of Nkx6.1 in neural cells at stages before the onset of Irx3 expression can induce ectopic MN generation (FIG. 5C).

Next examined was the fate of cells at levels of the neural axis where ectopic expression of Nkx6.1 occurred together with Irx3. Misexpression of Nkx6.1 at this level resulted in the ectopic generation of many Chx10$^+$ V2 neurons within the p0 and p1 domains (FIGS. 5Bix–5Bxi). Many ectopic Lim3$^+$ cells were also detected within these domains, some of which were mitotic progenitors (FIG. 5B viii). In addition, the ectopic expression of Nkx6.1 within the p0 and p1 domains resulted in a marked decrease in the number of En1$^+$ V1 (FIG. 5Bxi) and Evx1/2$^+$ V0 neurons (data not shown). Ectopic MN markers were not detected, suggesting that the coincident expression of Irx3 attenuates the ability of Nkx6.1 to induce MNs (FIG. 5B xii). Together, these results support the idea that Nkx6.1, in the context of Irx3 activity, promotes the generation of V2 neurons (FIG. 5C).

Misexpression of Irx3 Directs V2 Neuron Generation at the Expense of Motor Neurons To test more directly whether the expression of Irx3 in progenitor cells that express Nkx6.1 results in a switch from MN to V2 neuron fate, Irx3 was misexpressed in regions ventral to the p2 domain and the resulting pattern of neurogenesis was examined. Cells that ectopically expressed Irx3 failed to express the MN markers MNR2, Isl1/Isl2 or HB9 (FIGS. 6A and 6D and data not shown). Neighboring pMN cells that lacked ectopic Irx3 expression maintained expression of these MN markers (FIG. 6D), indicating the cell-autonomy of Irx3 action. In addition, V2 neurons, defined by Chx10 expression, were generated at markedly more ventral positions, within the normal domain of MN generation (FIGS. 6C and 6F). The pattern of Lim3 expression was not altered by ventral misexpression of Irx3 (FIG. 6B and 6E), consistent with the normal overlap of Lim3 and Irx3 expression within the p2 domain.

These findings, taken together with the results of late Nkx6.1 misexpression described above, indicate that coexpression of Irx3 and Nkx6.1 by ventral progenitor cells specifies V2 neuron identity. The domain of the ventral neural tube in which Nkx6.1 is able to generate MNs thus appears to be limited by the expression of Irx3 in cells dorsal to the p2/pMN domain boundary.

Nkx2.2 Constrains the Ability of Nkx6.1 to Induce Motor Neurons

Next examined was whether the expression of Nkx2.2 within the pMN domain is sufficient to repress MN generation. To test this Nkx2.2 was misexpressed in regions dorsal to the p3 domain and the resulting pattern of neurogenesis was examined. Detected was a marked repression in the expression of MNR2, Lim3, Isl1, Isl2 and HB9 in cells that expressed Nkx2.2 (FIG. 7A and data not shown). A few ectopic Nkx2.2-labeled cells that co-expressed HB9 were detected in a lateral position, characteristic of post-mitotic neurons (FIG. 7A). The coexpression of Nkx2.2 and MN markers in these cells is likely to reflect the late onset of expression of Nkx2.2, after cells have committed to a MN fate. These results show that Nkx2.2 activity is sufficient to repress MN differentiation, extending findings that Nkx2.2 activity within the p3 domain is required to suppress MN fate (Briscoe et al., 1999).

Nkx2.2 Expression Directs V3 Interneuron Generation

The role of Nkx2.2 in repressing MN generation raised the additional issue of whether Nkx2.2 activity is sufficient to generate V3 neurons. To test this the pattern of expression of the V3 neuron marker Sim1 in Nkx2.2-infected embryos was analyzed. Misexpression of Nkx2.2 directed the ectopic expression of Sim1 both within the domain of Nkx6.1 expression and throughout the dorsal neural tube (FIGS. 7Bi–7Biv). Nkx2.2 did not induce ectopic Nkx6.1 expression (data not shown), and Nkx6.1 was not sufficient to induce V3 neurons (FIGS. 7Bv and 7Bvi). Thus, Nkx2.2 is able to induce V3 neurons independently of Nkx6.1 activity. Nkx2.9 mimicked the ability of Nkx2.2 to induce V3 neurons (FIGS. 7Bvii and 7Bviii), supporting the idea that these two proteins have equivalent patterning activities. These findings, taken together with studies of Nkx2.2 mutant mice (Briscoe et al., 1999), establish the critical role of Nkx2.2 in suppressing MN and promoting V3 neuron fates.

Discussion

Figure 8:
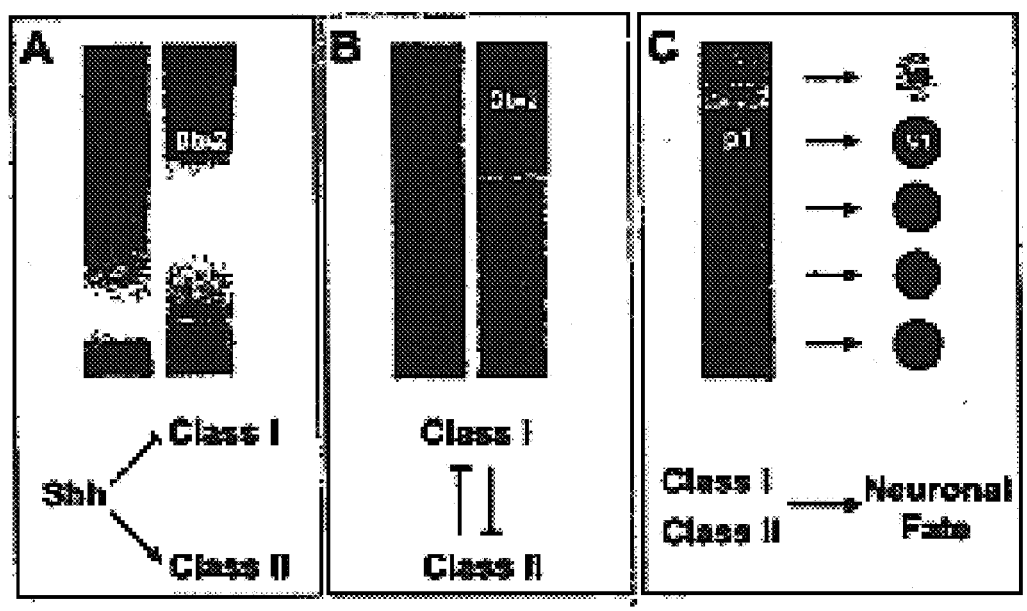

The results described in this series of experiments fit most easily into a three step model that links graded Shh signaling, the expression of class I and class II proteins by neural progenitor cells and the pattern of neuronal subtype generation in the ventral neural tube (FIG. 8). In a first step, the expression of progenitor cell homeodomain proteins is differentially repressed or activated by graded Shh signaling (FIG. 8A). In a second step, cross-repressive interactions between class I and class II proteins establish, refine and stabilize progenitor domains (FIG. 8B). In a third step, the profile of homeodomain proteins expressed within each progenitor domain directs the generation of specific sets of post-mitotic neurons (FIG. 8C). Each step of this model is discussed in the context of the interpretation of graded extracellular signals during the patterning of embryonic tissues.

Formation and Maintenance of Neural Progenitor Domains The findings herein address first the issue of how discrete progenitor domains are established in the ventral neural tube, in response to Shh signaling. A ventral to dorsal gradient of Shh signaling activity appears to have an initial role in defining the dorsoventral domains over which individual class I and class II proteins are expressed. Yet, the existence of an extracellular gradient of Shh activity does not offer an easy explanation for the sharp boundaries that exist between progenitor domains. These findings suggest that cross-repressive interactions that occur between class I and class II proteins may serve two early roles: first to establish the initial dorsoventral domains of class I and class II protein expression, and second to refine the initially imprecise pattern of homeodomain protein expression initiated by graded Shh signals. Support for this idea comes from the analysis of ventral patterning in mouse mutants lacking homeodomain protein function. The loss of Pax6 function leads to an expansion in the dorsoventral extent of the p3 domain, despite a constant level of Shh activity (Ericson et al., 1997a). Conversely, the loss of Nkx6.1 function results in a ventral expansion in the extent of the p1 domain, without any change in Shh signaling (Sander et al., submitted). It is noteworthy that the boundaries of each of the five progenitor domains are sharply defined, yet class II proteins have been identified only at the pMN/p3 and p1/p2 boundaries. Thus, additional class II proteins may exist, with patterns of expression that complement the three orphan class I proteins.

A second issue is how individual progenitor domains are maintained in relatively constant proportions over time. As neuronal fates are established, ventral progenitor cells undergo multiple rounds of proliferation (Langman et al., 1966) and the dorsoventral extent of the ventral neural tube increases markedly in size. Thus, the level of Shh activity at a given position in the ventral neural tube is likely to change significantly over time. The findings herein show that by stage 15, ventral progenitor domains can be maintained despite the loss of Shh signaling. The cross-repressive interaction between class I and class II proteins may help to maintain progenitor domains over time, in the face of a changing level of Shh activity. The findings suggest that these cross-repressive interactions relieve progenitor cells of a requirement for ongoing Shh signaling but do not exclude that Shh has a later role in regulating the proliferation of cells within individual progenitor domains (Rowitch et al., 1999).

How do neural progenitor cells initially perceive the extracellular gradient of Shh activity? Several components of the vertebrate hedgehog signaling pathway have been identified (Ingham, 1998). In particular, two zinc finger transcription factors, Gli1 and Gli2, have been proposed as intermediaries in Shh signaling (Ruiz i Altaba, 1999). One view of the initial steps in Shh signal transduction argues that the level of Gli activity varies in proportion to the concentration of extracellular Shh (Ingham, 1998), and thus different levels of Gli activity may repress or activate different class I and class II homeobox genes. However, ventral neuronal pattern is surprisingly normal in mice containing mutations in both the Gli1 and Gli2 genes (Ding et al., 1998; Matise et al., 1998). These findings raise the possibility (see Krishnan et al., 1997; Lewis et al., 1999) that additional transcriptional mediators participate in the initial interpretation of graded Shh signals within ventral progenitor cells.

The uncertainty that persists about the initial stages of Shh signal transduction in neural cells also leaves unresolved the issue of whether Shh acts independently to repress class I and to activate class II genes. The pairs of class I and class II proteins that form complementary domain boundaries are potent repressors of each other's expression. Thus, the repression of class I genes by Shh could depend on the activation of class II gene expression. Alternatively, the requirement for class II protein expression on Shh signaling may depend on the Shh repression of class I protein expression. A similar derepression mechanism has been suggested to operate during Drosophila development, in the dpp-mediated patterning of imaginal disc cells (Campbell and Tomlinson, 1999; Jazwinska et al., 1999; Minami et al., 1999).

The cross-regulatory interactions revealed for class I and class II proteins also have implications for the lineage relationship of neurons generated in the ventral neural tube. Lineage tracing studies have reported a temporal change in the extent to which clonally-related cells disperse along the dorsoventral axis of the ventral neural tube (Leber and Sanes, 1995). After early stage marking of ventral progenitors, clonally-related progeny spread widely along the dorsoventral axis of the ventral neural tube and acquire different neuronal identities (Leber and Sanes, 1995; Erskine et al., 1998). But, the progeny of clones marked at later developmental stages are restricted to narrower dorsoventral domains, and within these domains cells acquire more uniform neuronal fates (Leber and Sanes, 1995). The timing of the cross-regulatory interactions between class I and class II proteins that seem to confer progenitor domain identity matches well with the time of restriction in clonal cell dispersal, suggesting a causal relationship between these two processes. The homeodomain proteins that define an individual ventral progenitor domain could control the surface properties of progenitor cells and restrict their intermixing along the dorsoventral axis, in a manner analogous with mechanisms that establish segmental domains along the rostrocaudal axis of the hindbrain (Lumsden and Krumlauf, 1996; Xu et al., 1999).

Control of Neuronal Identity by a Homeodomain Protein Code.

This study has relied on ectopic expression methods to address the roles of Nkx6.1, Nkx2.2 and Irx3 in specifying the fate of V2 neurons, MNs and V3 neurons. The results herein show that Nkx2.2 activity is sufficient to induce V3 neurons, that Nkx6.1 activity in the absence of Irx3 induces MNs, whereas Nkx6.1 activity in the presence of Irx3 induces V2 neurons. The inferences derived from these gain-of-function studies are supported by the switches in neuronal fate that occur in mice in which individual class I and class II proteins have been inactivated by gene targeting. In mice lacking Pax6 activity, the dorsal expansion in the domain of Nkx2.2 expression is accompanied by an expansion in the domain of V3 neuron generation, and by the loss of MNs (Ericson et al., 1997a). Conversely, the loss of Nkx2.2 results in the loss of V3 neurons and in the ectopic generation of MNs within the p3 domain (Briscoe et al., 1999). In addition, the loss of Nkx6.1 activity depletes the ventral neural tube of many MNs and V2 neurons (Sander et al., submitted).

How do class I and class II proteins control neuronal subtype identity? The final cell division of certain ventral progenitors is accompanied by the onset of expression of a distinct set of homeodomain proteins, notably MNR2 and Lim3 (Tanabe et al., 1995; Ericson et al., 1997; Sharma et al., 1998). Ectopic expression of MNR2 is able to induce MN differentiation independent of dorsoventral position, and ectopic expression of Lim3 induces V2 neurons (Tanabe et al., 1998). The studies herein indicate that class I and class II proteins function upstream of MNR2 and Lim3. Thus within the pMN and p2 domains, the actions of progenitor homeodomain proteins in specifying neuronal subtype identity are likely to be mediated through MNR2 and Lim3. Subtype determinant factors with equivalent functions may therefore be expressed by cells in the other ventral progenitor domains.

These findings provide further support for the idea that the activity of individual homeodomain proteins can direct specific neuronal fates in the developing spinal cord. It is shown here that Nkx2.2 can specify V3 neuronal identity. In previous studies MNR2 has been shown to specify MN identity and Lim3 to direct V2 neuronal identity (Tanabe et al., 1998). Thus, the fate of other classes of neurons in the ventral spinal cord, and perhaps in other regions of the vertebrate central nervous system, may be controlled through the actions of similarly dedicated transcription factors. The activities of Nkx6.1 revealed in these studies also provide a further insight into the hierarchical functions of homeodomain proteins in specifying spinal MN identity. Nkx6.1 can induce the expression of both MNR2 and Lim3 in MN progenitors, and like MNR2, is able to specify MN fate in dorsal neural tube cells. Thus, it seems possible that Nkx6.1 functions upstream of MNR2 in a linear pathway of MN generation in the chick embryo.

Linking Graded Extracellular Signals to Neuronal Subtype Diversity

A set of seven homeodomain proteins defines five neural progenitor domains with a fundamental role in the organization of ventral neural pattern. The analysis of these homeodomain proteins suggests that ventral patterning proceeds in three stages: (1) the regulation of class I and class II proteins by graded Shh signals, (2) the refinement and maintenance of progenitor domain identity by cross-repressive interactions between homeodomain proteins, and (3) the translation of a homeodomain protein code into neuronal subtype identity. The central features of this model may apply to other vertebrate tissues in which cell pattern is regulated by local sources of extrinsic signals. Consistent with this idea, cross-regulatory interactions between transcription factors have been suggested to refine cell pattern in the embryonic mesoderm and in the pituitary gland (Papin and Smith, 2000; Dasen and Rosenfeld, 1999)

Finally, it is noted that the principles of the model of ventral patterning outlined here resemble those involved in subdividing the Drosophila embryo (Lawrence, 1992). Graded Shh signaling subdivides the ventral neural tube into five domains, just as graded levels of the dorsal protein establish five distinct regions of the early Drosophila embryo (Huang et al., 1997), suggesting an upper limit to the number of distinct cell fates that can be generated in response to a single gradient signaling system. In addition, the graded anteroposterior distribution of maternally-supplied factors in the Drosophila embryo is known to initiate the expression of a set of proteins encoded by the gap genes (Struhl et al., 1992). Subsequent cross-regulatory interactions establish and maintain sharp boundaries in the expression of gap proteins, and their activities within individual domains control later aspects of cell pattern (Kraut and Levine, 1991; Wu et al., 1998). Thus in the neural tube and the Drosophila embryo, the cross-repression of genes whose initial expression is controlled by graded upstream signals provides an effective mechanism for establishing and maintaining progenitor domains and for imposing cell type identity.

REFERENCES FOR FIRST SERIES OF EXPERIMENTS

Arber, S., Han, B., Mendelsohn, M., Smith, M., Jessell, T. M., and Sockanathan, S. (1999). Requirement for the homeobox gene Hb9 in the consolidation of motor neuron identity. Neuron 23, 659–674.

Briscoe, J., Sussel, L., Serup, P., Hartigan-O'Connor, D., Jessell, T. M., Rubenstein, J. L., and Ericson, J. (1999). Homeobox gene Nkx2.2 and specification of neuronal identity by graded Sonic hedgehog signalling. Nature 398, 622–622.

Campbell, G., and Tomlinson, A. (1999). Transducing the Dpp morphogen gradient in the wing of Drosophila: is regulation of Dpp targets by brinker. Cell 96, 553–562.

Chiang, C., Litingtung, Y., Lee, E., Young, K. E., Corden, J. L., Westphal, H., and Beachy, P. A. (1996). Cyclopia and defective axial patterning in mice lacking Sonic hedgehog gene function. Nature 383, 407–413.

Dasen, J. S., and Rosenfeld, M. G. (1999). Combinatorial codes in signaling and synergy: lessons from pituitary development. Curr. Opin. Genet. Dev. 9, 566–574.

Ding, Q., Motoyama, J., Gasca, S., Mo, R., Sasaki, H., Rossant, J., and Hui, C. C. (1998). Diminished Sonic hedgehog signaling and lack of floor plate differentiation in Gli2 mutant mice. Development 125, 2533–2543.

Ericson, J., Morton, S., Kawakami, A., Roelink, H., and Jessell, T. M. (1996). Two critical periods of Sonic Hedgehog signaling required for the specification of motor neuron identity. Cell 87, 661–673.

Ericson, J., Rashbass, P., Schedl, A., Brenner-Morton, S., Kawakami, A., van Heyningen, V., Jessell, T. M., and Briscoe, J. (1997a). Pax6 controls progenitor cell identity and neuronal fate in response to graded Shh signaling. Cell 90, 169–180.

Ericson, J., Briscoe, J., Rashbass, P., van Heyningen, V., and Jessell, T. M. (1997b). Graded sonic hedgehog signaling and the specification of cell fate in the ventral neural tube. Cold Spring Harb. Symp. Quant. Biol. 62, 451–466.

Erskine, L., Patel, K., and Clarke, J. D. (1998). Progenitor dispersal and the origin of early neuronal phenotypes in the chick embryo spinal cord. Dev. Biol. 199, 26–41.

Funayama, N., Sato, Y., Matsumoto, K., Ogura, T., and Takahashi, Y. (1999). Coelom formation: binary decision of the lateral plate mesoderm is controlled by the ectoderm. Development 126, 4129–4138.

Goulding M. D., Lumsden A., and Gruss P. (1993). Signals from the notochord and floor plate regulate the region-specific expression of two Pax genes in the developing spinal cord. Development 117, 1001–1016

Hamburger, V., and Hamilton, H. L. (1951). A series of normal stages in the development of the chick embryo. J. Morphol. 88, 49–92.

Huang, A. M., Rusch, J., and Levine, M. (1997). An anteroposterior Dorsal gradient in the Drosophila embryo. Genes Dev. 11, 1963–1973.

Hughes, S. H., Greenhouse, J. J., Petropoulos, C. J., and Sutrave, P. (1987). Adaptor plasmids simplify the insertion of foreign DNA into helper-independent retroviral vectors. J. Virol. 61, 3004–3012.

Ingham, P. W. (1998). Transducing Hedgehog: the story so far. EMBO J. 17, 3505–3511.

Jazwinska, A., Kirov, N., Wieschaus, E., Roth, S., and Rushlow, C. (1999). The Drosophila gene brinker reveals a novel mechanism of Dpp target gene regulation. Cell 96, 563–573.

Kraut, R., and Levine, M. (1991). Spatial regulation of the gap gene giant during Drosophila development. Development 111, 601–609.

Krishnan, V., Pereira, F. A., Qiu, Y., Chen, C. H., Beachy, P. A., Tsai, S. Y., and Tsai, M. J. (1997). Mediation of Sonic hedgehog-induced expression of COUP-TFII by a protein phosphatase. Science 278, 1947–1950.

Langman, J., Guerrant, R. L., and Freeman, G. G. (1966). Behavior of neuroepithelial cells during closure of neural tube. J. Comp. Neurol. 127, 399–411.

Lawrence, P. (1992). The Making of a Fly. Oxford, Blackwell Scientific.

Lawrence, P. A., and Struhl, G. (1996). Morphogens, compartments, and pattern: lessons from drosophila? Cell 85, 951–961.

Leber, S. M., and Sanes, J. R. (1995). Migratory paths of neurons and glia in the embryonic chick spinal cord. J Neurosci. 15, 1236–1248.

Lewis, K. E., Drossopoulou, G., Paton, I. R., Morrice, D. R., Robertson, K. E., Burt, D. W., Ingham, P. W., and Tickle, C. (1999). Expression of ptc and gli genes in talpid3 suggests bifurcation in Shh pathway. Development 126, 2397–2407.

Lumsden, A., and Krumlauf, R. (1996). Patterning the vertebrate neuraxis. Science 274, 1109–1115.

Mansouri, A., and Gruss, P. (1998). Pax3 and Pax7 are expressed in commissural neurons and restrict ventral neuronal identity in the spinal cord. Mech. Dev. 78, 171–178.

Marti, E., Takada, R., Bumcrot, D. A., Sasaki, H., and McMahon, A. P. (1995). Distribution of Sonic hedgehog peptides in the developing chick and mouse embryo. Development 121, 2537–2547.

Matise, M. P., Epstein, D. J., Park, H. L., Platt, K. A., and Joyner, A. L. (1998). Gli2 is required for induction of floor plate and adjacent cells, but not most ventral neurons in the mouse central nervous system. Development 125, 2759–2770.

McDowell, N., and Gurdon, J. B. (1999). Activin as a morphogen in Xenopus mesoderm induction. Semin. Cell Dev. Biol. 10, 311–317.

Minami, M., Kinoshita, N., Kamoshida, Y., Tanimoto, H., and Tabata, T. (1999). Brinker is a target of Dpp in Drosophila that negatively regulates Dpp-dependent genes. Nature 398, 242–246.

Morgan, B. A., and Fekete, D. M. (1996). Manipulating gene expression with replication-competent retroviruses. Methods Cell Biol. 51, 185–218.

Muramatsu, T., Mizutani, Y., Ohmori, Y., and Okumura, J. (1997). Comparison of three nonviral transfection methods for foreign gene expression in early chicken embryos in ovo. Biochem. Biophys. Res. Commun. 230, 376–380.

Pabst, O., Herbrand, H., and Arnold, H. H. (1998). Nkx2.9 is a novel homeobox transcription factor which demarcates ventral domains in the developing mouse CNS. Mech. Dev. 73, 85–93.

Papin, C., and Smith, J. C. (2000). Gradual refinement of activin-induced thresholds requires protein synthesis. Dev. Biol. 217, 166–172.

Pierani, A., Brenner-Morton, S., Chiang, C., and Jessell, T. M. (1999). A sonic hedgehog-independent, retinoid-activated pathway of neurogenesis in the ventral spinal cord. Cell 97, 903–915.

Qiu, M., Shimamura, K., Sussel, L., Chen, S., and Rubenstein, J. L. (1998). Control of anteroposterior and dorsoventral domains of Nkx-6.1 gene expression relative to other Nkx genes during vertebrate CNS development. Mech. Dev. 72, 77–88.

Roelink, H., Porter, J. A., Chiang, C., Tanabe, Y., Chang, D. T., Beachy, P. A., and Jessell, T. M. (1995). Floor plate and motor neuron induction by different concentrations of the amino-terminal cleavage product of sonic hedgehog autoproteolysis. Cell 81, 445–455.

Rowitch, D. H., S.-Jacques. B., Lee, S. M., Flax, J. D., Snyder, E. Y., and McMahon, A. P. (1999). Sonic hedgehog regulates proliferation and inhibits differentiation of CNS precursor cells. J. Neurosci. 19, 8954–8965.

Ruiz i Altaba, A. (1999). Gli proteins and Hedgehog signaling: development and cancer. Trends Genet. 15, 418–425.

Sander, M., Paydar, S., Ericson, J., Briscoe, J., German, M., Jessell, T. M., and Rubenstein, J. L. R. (2000). Ventral Neural Tube Patterning by Nkx Homeobox Genes: Nkx6.1 Controls Somatic Motor Neuron and Ventral Interneuron Fates. Submitted.

Schaeren-Wiemers, N., and Gerfin-Moser, A. (1993). A single protocol to detect transcripts of various types and expression levels in neural tissue and cultured cells: in situ hybridization using digoxigenin-labelled cRNA probes. Histochemistry 100, 431–440.

Sharma, K., Sheng, H. Z., Lettieri, K., Li, H., Karavanov, A., Potter, S., Westphal, H., and Pfaff, S. L. (1998). LIM homeodomain factors Lhx3 and Lhx4 assign subtype identities for motor neurons. Cell 95, 817–828.

Smith, J. C. (1995). Mesoderm-inducing factors and mesodermal patterning. Curr. Opin. Cell Biol. 7, 856–861.

Struhl, G., Johnston, P., and Lawrence, P. A. (1992). Control of Drosophila body pattern by the hunchback morphogen gradient. Cell 69, 237–249

Tanabe, Y., William, C., and Jessell, T. M. (1998). Specification of motor neuron identity by the MNR2 homeodomain protein. Cell 95, 67–80.

Wolpert, L. (1969). Positional information and the spatial pattern of cellular differentiation. J. Theor. Biol. 25, 1–47.

Wu, X., Vakami, R., and Small, S. (1998). Two distinct mechanisms for differential positioning of gene expression borders involving the Drosophila gap protein giant. Development 125, 3765–3774.

Xu, Q., Mellitzer, G., Robinson, V., and Wilkinson, D. G. (1999). In vivo cell sorting in complementary segmental domains mediated by Eph receptors and ephrins. Nature 399, 267–271.

Yamada, T., Pfaff, S. L., Edlund, T., and Jessell, T. M. (1993). Control of cell pattern in the neural tube: motor neuron induction by diffusible factors from notochord and floor plate. Cell 73, 673–686.

Second Series of Experiments

During the development of the embryonic central nervous system (CNS) the mechanisms that specify regional identity and neuronal fate are intimately linked (1,2). In the ventral half of the CNS, for example, the secreted factor Sonic hedgehog (Shh) has a fundamental role in controlling both regional pattern and neuronal fate (3). The genetic programs activated in neural progenitor cells in response to Shh signaling, however, remain poorly defined. Emerging evidence suggests that homeobox genes function as critical intermediaries in the neural response to Shh signals (1–3). In particular, genetic studies in mice have shown that two Shh-regulated homeobox genes, Nkx2.1 and Nkx2.2, control dorsoventral fates both in the basal telencephalon and in the ventral-most regions of the spinal cord (4, 5). These findings raise the possibility that members of the Nkx class of homeobox genes have a central role in imposing regional pattern and neuronal fate in the ventral region of the CNS.

A recently identified Nkx gene, Nkx6.1, is expressed by neural progenitor cells throughout the ventral third of the neural tube (5–7), suggesting that it may have a pervasive role in ventral neural patterning. To define the role of Nkx6.1 in neural development, patterns of neurogenesis were compared in the embryonic spinal cord and hindbrain of wild type mice and mice lacking Nkx6.1 (8). In wild type embryos, neural expression of Nkx6.1 is first detected at spinal cord and caudal hindbrain levels at ~e8.5 (data not shown; ref 6) and by e9.5 the gene is expressed throughout the ventral third of the neural tube (FIG. 9A). The expression of Nkx6.2 persists until at least e12.5 (FIGS. 9B, 9C; and data not shown). Nkx6.1 expression was also detected in mesodermal cells flanking the ventral spinal cord (FIGS. 9B, 9C). To define more precisely the domain of expression of Nkx6.1 compared was Nkx6.1 expression with that of nine homeobox genes—Pax3, Pax7, Gsh1, Gsh2, Pax6, Dbx1, Dbx1, Dbx2 and Nkx2.9—that have been shown to define discrete progenitor cell domains along the dorsoventral axis of the ventral neural tube (9–14).

This analysis revealed that the dorsal boundary of Nkx6.1 expression is positioned ventral to the boundaries of four genes expressed by dorsal progenitor cells: Pax3, Pax7, Gsh1 and Gsh2 (FIGS. 9I, 9N; and data not shown). Within the ventral neural tube, the dorsal boundary of Nkx6.1 expression is positioned ventral to the domain of Dbx1 expression and close to the ventral boundary of Dbx2 expression (FIGS. 9G, 9H, and 9P). The domain of Pax6 expression extends ventrally into the domain of Nkx6.1 expression (FIG. 9O), whereas the expression of Nkx2.2 and Nkx2.9 overlaps with the ventral-most domain of Nkx6.1 expression (FIGS. 9O, 9Q).

To address the function of Nkx6.1 in neural development, progenitor cell identity and the pattern of neuronal differentiation in Nkx6.1 null mutant mice was analyzed (8). Detected was a striking change in the profile of expression of three homeobox genes, Dbx2, Gsh1 and Gsh2, in Nkx6.1 mutants. The domains of expression of Dbx2, Gsh1 and Gsh2 each expanded into the ventral neural tube (FIGS. 9K–9M; and data not shown). At e10.5, Dbx2 was expressed at high levels by progenitor cells adjacent to the floor plate, but at this stage ectopic Dbx2 expression was detected only at low levels in regions of the neural tube that generate motor neurons (FIG. 9K). By e12.5, however, the ectopic ventral expression of Dbx2 had become more uniform, and now clearly included the region of motor neuron and V2 neuron generation (FIG. 9L). Similarly, in Nkx6.1 mutants, both Gsh1 and Gsh2 were ectopically expressed in a ventral domain of the neural tube, and also in adjacent paraxial mesodermal cells (FIG. 9M; data not shown).

The ventral limit of Pax6 expression was unaltered in Nkx6.1 mutants, although the most ventrally located cells within this progenitor domain expressed a higher level of Pax6 protein than in wild type embryos (FIGS. 9O, 9S). No change was detected in the patterns of expression of Pax3, Pax7, Dbx1, Nkx2.2 or Nkx2.9 in Nkx6.1 mutant embryos (FIGS. 9R–9U; and data not shown). Importantly, the level of Shh expression by floor plate cells was unaltered in Nkx6.1 mutants (FIGS. 9N and 9R). Thus, the loss of Nkx6.1 function deregulates the patterns of expression of a selected subset of homeobox genes in ventral progenitor cells, without an obvious effect on Shh levels (FIGS. 9D, 9E). The role of Shh in excluding Dbx2 from the most ventral region of the neural tube (11) appears therefore to be mediated through the induction of Nkx6.1 expression. Consistent with this view, ectopic expression of Nkx6.1 represses Dbx2 expression in chick neural tube (12). The detection of sites of ectopic Gsh1/2 expression in the ventral neural tube as well as the paraxial mesoderm, both sites of Nkx6.1 expression, suggests that Nkx6.1 has a general role in restricting Gsh1/2 expression. The signals that promote ventral Gsh1/2 expression in Nkx6.1 mutants remain unclear, but could involve factors other than Shh that are secreted by the notochord (15).

The domain of expression of Nkx6.1 within the ventral neural tube of wild type embryos encompasses the progenitors of three main neuronal classes: V2 interneurons, motor neurons and V3 interneurons (5, 6, 10–13) (FIGS. 10A–10D). It was examined whether the generation of any of these neuronal classes is impaired in Nkx6.1 mutants, focusing first on the generation of motor neurons. In Nkx6.1 mutant embryos there was a marked reduction in the number of spinal motor neurons, as assessed by expression of the homeodomain proteins Lhx3, Isl1/2 and HB9 (16, 17) (FIGS. 10E–10L), and by expression of the gene encoding the transmitter synthetic enzyme choline acetyltransferase (data not shown). In addition, few if any axons were observed emerging from the ventral spinal cord (data not shown). The incidence of motor neuron loss, however, varied along the rostrocaudal axis of the spinal cord. Few if any motor neurons were detected at caudal cervical and upper thoracic levels of Nkx6.1 mutants analyzed at e11–e12.5 (FIGS. 10M, 10N, 10Q, 10R), whereas motor neuron number was reduced only by 50–75% at more caudal levels (FIGS. 10O, 10P, 10S, 10T; and data not shown). At all axial levels, the initial reduction in motor neuron number persisted at both e12.5 and p0 (FIGS. 10M–10T and data not shown), indicating that the loss of Nkx6.1 activity does not simply delay motor neuron generation. Moreover, no increase was detected in the incidence of TUNEL$^+$ cells in Nkx6.1 mutants (data not shown), indicating that the depletion of motor neurons is not the result of apoptotic death.

The persistence of some spinal motor neurons in Nkx6.1 mutants raised the possibility that the generation of particular subclasses of motor neurons is selectively impaired. To address this issue, the expression of markers of distinct subtypes of motor neurons at both spinal and hindbrain levels of Nkx6.1 mutant embryos was monitored. At spinal levels, the extent of the reduction in the generation of motor neurons that populate the median (MMC) and lateral (LMC) motor columns was similar in Nkx6.1 mutants, as assessed by the number of motor neurons that coexpressed Isl1/2 and Lhx3 (defining MMC neurons, refs 16, 17) (FIGS. 11A, 11B) and by the expression of Raldh2 (defining LMC neurons, refs. 17, 18) (FIGS. 11C, 11D). In addition, the generation of autonomic visceral motor neurons was reduced to an extent similar to that of somatic motor neurons at thoracic levels of the spinal cord of e12.5 embryos (data not shown). Thus, the loss of Nkx6.1 activity depletes the major subclasses of spinal motor neurons to a similar extent.

At hindbrain levels, Nkx6.1 is expressed by the progenitors of both somatic and visceral motor neurons (FIGS. 11E, 11F; and data not shown). Therefore, it was examined whether the loss of Nkx6.1 might selectively affect subsets of cranial motor neurons. Detected was a virtually complete loss in the generation of somatic motor neurons (hypoglossal and abducens) in Nkx6.1 mutants, as assessed by the absence of dorsally generated HB9$^+$ motor neurons (FIGS. 11G, 11H; and data not shown, refs 5, 17). In contrast, there was no change in the initial generation of any of the cranial visceral motor neuron populations, assessed by coexpression of Isl1 and Phox2a (5, 19) within ventrally generated motor neurons (FIGS. 11I, 11J; and data not shown). Moroever, at rostral cervical levels, the generation of spinal accessory motor neurons (10) was also preserved in Nkx6.1 mutants (data not shown). Thus, in the hindbrain the loss of Nkx6.1 activity selectively eliminates the generation of somatic motor neurons, while leaving visceral motor neurons intact. Cranial visceral motor neurons, unlike spinal visceral motor neurons, derive from progenitors that express the related Nkx genes Nkx2.2 and Nkx2.9 (5). The preservation of cranial visceral motor neurons in Nkx6.1 mutant embryos may therefore reflect the dominant activities of Nkx2.2 and Nkx2.9 within these progenitor cells.

Next examined was whether the generation of ventral interneurons is affected by the loss of Nkx6.1 activity. V2 and V3 interneurons are defined, respectively, by expression of Chx10 and Sim1 (5, 17) (FIGS. 12A, 12G). A severe loss of Chx10 V2 neurons was detected in Nkx6.1 mutants at spinal cord levels (FIG. 12B), although at hindbrain levels of Nkx6.1 mutants ~50% of V2 neurons persisted (data not shown). In contrast, there was no change in the generation of Sim1 V3 interneurons at any axial level of Nkx6.1 mutants (FIG. 12H). Thus, the elimination of Nkx6.1 activity affects the generation of only one of the two major classes of ventral interneurons that derive from the Nkx6.1 progenitor cell domain.

Evx1$^+$, Pax2$^+$ V1 interneurons derive from progenitor cells located dorsal to the Nkx6.1 progenitor domain, (FIG. 12B) within a domain that expresses Dbx2, but not Dbx1 (11, 20, 21). Since Dbx2 expression undergoes a marked ventral expansion in Nkx6.1 mutants, it was examined whether there might be a corresponding expansion in the domain of generation of V1 neurons. In Nkx6.1 mutants, the region that normally gives rise to V2 neurons and motor neurons now also generated V1 neurons, as assessed by the ventral shift in expression of the En1 and Pax2 homeodomain proteins (FIGS. 12B, 12C, 12E, 12F). Consistent with this, there was a 2–3 fold increase in the total number of V1 neurons generated in Nkx6.1 mutants (FIGS. 12C, 12D). In contrast, the domain of generation of Evx1/2 V0 neurons, which derive from the Dbx1 progenitor domain (11), was unchanged in Nkx6.1 mutants (FIGS. 12I, 12J). Thus, the ventral expansion in Dbx2 expression is accompanied by a selective switch in interneuronal fates, from V2 neurons to V1 neurons. In addition, it was observed that some neurons within the ventral spinal cord of Nkx6.1 mutants coexpressed the V1 marker En1 and the V2 marker Lhx3 (FIGS. 12K, 12L). The coexpression of these markers is rarely if ever observed in single neurons in wild type embryos (22). Thus, within individual neurons in Nkx6.1 mutants, the ectopic program of V1 neurogenesis appears to be initiated in parallel with a residual, albeit transient, program of V2 neuron generation. This result complements observations in Hb9 mutant mice, in which the programs of V2 neuron and motor neuron generation coincide transiently within individual neurons (17, 23).

Taken together, the findings herein reveal an essential role for the Nkx6.1 homeobox gene in the specification of regional pattern and neuronal fate in the ventral half of the mammalian CNS. Within the broad ventral domain within which Nkx6.1 is expressed (FIG. 13A), its activity is required to promote motor neuron and V2 interneuron generation and to restrict the generation of V1 interneurons (FIG. 13B). The loss of motor neurons and V2 neurons could be a direct consequence of the loss of Nkx6.1 activity, since the depletion of these two neuronal subtypes is evident at stages when only low levels of Dbx2 are expressed ectopically in most regions of the ventral neural tube. Consistent with this view, the ectopic expression of Nkx6.1 is able to induce both motor neurons and V2 neurons in chick neural tube (12). V3 interneurons and cranial visceral motor neurons derive from a set of Nkx6.1 progenitors that also express Nkx2.2 and Nkx2.9 (5) (FIG. 13A). The generation of these two neuronal subtypes is unaffected by the loss of Nkx6.1 activity, suggesting that the actions of Nkx2.2 and Nkx2.9 dominate over that of Nkx6.1 within these progenitors. The persistence of some spinal motor neurons and V2 neurons in Nkx6.1 mutants could reflect the existence of a functional homologue within the caudal neural tube.

The role of Nkx6.1 revealed in these studies, taken together with previous findings (4, 5), suggests a model in which the spatially restricted expression of Nkx genes within the ventral neural tube (FIG. 13) has a pivotal role in defining the identity of ventral cell types induced in response to graded Shh signaling. Strikingly, in Drosophila, the Nkx gene NK2 has been shown to have an equivalent role in specifying neuronal fates in the ventral nerve cord (24). Moreover, the ability of Nkx6.1 to function as a repressor of the dorsally expressed Gsh1/2 homeobox genes parallels the ability of Drosophila NK2 to repress Ind, a Gsh1/2-like homeobox gene (25). Thus, the evolutionary origin of regional pattern along the dorsoventral axis of the central nervous system may predate the divergence of invertebrate and vertebrate organisms.

REFERENCES AND NOTES FOR SECOND SERIES OF EXPERIMENTS

20. J. L. Rubenstein et al., *Annu Rev Neurosci.* 21, 45–77 (1998); S. A. Anderson, D. D. Eisenstat, L. Shi, J. L. Rubenstein, *Science* 278, 474–476 (1997)

2. A. Lumsden, R. Krumlauf, *Science* 274, 1109–15 (1996).
3. Y. Tanabe, T. M. Jessell, *Science* 274, 1115–23 (1996); M. Hammerschmidt, A. Brook, A. P. McMahon *Trends Genet.* 13, 14–21 (1997); J. Ericson, et al., *Cold Spring Harb. Symp. Quant. Biol.* 62, 451–66 (1997).
4. L. Sussel, O. Marin, S. Kimura, J. L. Rubenstein, *Development* 126, 3359–70 (1999).
5. J. Briscoe, et al., *Nature* 398, 622–7 (1999).
6. M. Qiu, K. Shimamura, L. Sussel, S. Chen, J. L. Rubenstein, *Mech. Dev.* 72, 77–88 (1998).
7. O. Pabst, H. Herbrand, H. H. Arnold, *Mech. Dev.* 73, 85–93 (1998).
8. M. Sander et al., submitted (2000). A null mutation in Nkx6.1 was generated by gene targeting in 129-strain ES cells. Briefly, a 800 bp NotI fragment containing part of exon1 was excised and replaced by a PGK-neo cassette. Mice were genotyped by Southern blotting of EcoRI digested genomic DNA with a 3' external probe to the targeting construct. The size of the wild-type allele is 10 kb, and of the targeted allele 4.3 kb. The mice were outcrossed with C57B16. Heterozygotes appeared normal, whereas homozygous mutant embryos (which are born at Mendelian frequency) died soon after birth. Newborn mutants were slightly smaller (~85% normal weight), exhibited a persistently flexed body posture and lacked spontaneous movements. Tactile stimulation elicited weak movements of their extremities but no movement of their trunk was detected.
9. Localization of mRNA was performed by in situ hybridization following the method of Schaeren-Wiemers and Gerfin-Moser; Histochemistry 100, 431 (1993). The Dbx2 riboprobe comprised the 5' EcoR1 fragment of the mouse cDNA; (11). Probes for other cDNAs were used as described: Nkx2.9 (5), Nkx6.1 (6), Dbx1 (11), Gsh1 (14), Gsh2 (14), Pax3 (13), Chx10 (10), Sim1 (5), En1 (11, 20, 21), Evx1 (11, 21) and RALDH2 (18). Protein expression was localized by indirect fluorescence immunocytochemistry or peroxidase immunohistochemistry (3, 5). Nkx6.1 was detected with a rabbit antiserum (5). Antisera against Shh, Pax7, Isl1/2, HB9, Lhx3, Chx10, Phox2a/b, En1, Pax2 have been described (5, 10). Fluorescence detection was carried out using an MRC 1024 Confocal Microscope.
10. J. Ericson, et al., Cell. 90, 169–80 (1997).
11. A. Pierani, S. Brenner-Morton, C. Chiang, T. M. Jessell, *Cell* 97, 903–15 (1999).
12. J. Briscoe et al., submitted (2000).
13. M. D. Goulding et al., *EMBO J.* 10, 1135–47 (1991).
14. M. T. Valerius, H. Li, J. L. Stock, M. Weinstein, S. Kaur, G. Singh, S. S. Potter, Dev. Dyn. 203, 337–51 (1995).
15. M. Hebrok, S. K. Kim, D. A. Melton, *Genes Dev.* 12, 1705–13 (1998).
16. T. Tsuchida, et al., *Cell* 79, 957–70 (1994).
17. S. Arber, B. Han, M. Mendelsohn, M. Smith, T. M. Jessell, S. Sockanathan, *Neuron* 23, 659–74 (1999).
18. S. Sockanathan, T. M. Jessell, *Cell* 94, 503–14 (1998).
19. A. Pattyn, X. Morin, H. Cremer, C. Goridis, J. F. Brunet, *Development* 124, 4065–75 (1997).
20. M. P. Matise, A. L. Joyner, *J. Neurosci.* 17, 7805–16 (1998).
21. J. D. Burrill, L. Moran, M. D. Goulding, H. Saueressig, *Development* 124, 4493–503 (1997).
22. J. Ericson et al., *Cell* 87, 661–73 (1996).
23. J. Thaler et al., *Neuron* 23, 675–87 (1999).
24. J. A. McDonald, S. Holbrook, T. Isshiki, J. Weiss, C. Q. Doe, D. M. Mellerick. *Genes Dev.* 12, 3603–12 (1998). H. Chu; C. Parras; K. White; F. Jimenez, *Genes and Development.* 12, 3613–24 (1998).
25. J. B. Weiss, T. Von Ohlen, D. M. Mellerick, G. Dressier, C. Q. Doe, M. P. Scott, *Genes Dev.* 12, 3591–602 (1998).
26. We thank the following people for cDNAs: P. Gruss (Pax3), S. Potter (Gsh1&2), F. Ruddle (Dbx1), R. McInnes (Chx10), A. Joyner (En1), G. Martin (Evx1), M. Tessier-Lavigne (Sim1), C. Gall (ChAT); and the following people for antibodies: J. F. Brunet (anti-Phox2), H. Westphal (Lhx3).

What is claimed is:

1. A neural stem cell which does not express homeodomain transcription factor Irx3 protein or homeodomain transcription factor Nkx2.2 protein comprising a retroviral expression system, wherein the retroviral expression system expresses homeodomain transcription factor Nkx6.1 protein.

2. The neural stem cell of claim 1, wherein the neural stem cell is a mammalian neural stem cell.

3. The neural stem cell of claim 2, wherein the mammalian neural stem cell is a human neural stem cell.

4. A method of determining whether a chemical compound affects the generation of a motor neuron from a neural stem cell which comprises:

a) contacting the neural stem cell of claim 1 with the chemical compound under conditions such that in the absence of the compound the neural stem cell expresses homeodomain transcription factor Nkx6.1 protein and generates a motor neuron; and b) determining whether a motor neuron is generated, so as to thereby determine whether the chemical compound affects the generation of a motor neuron.

5. The method of claim 4, wherein the chemical compound promotes generation of the motor neuron.

* * * * *